United States Patent [19]

Bitonti

[11] Patent Number: 5,693,674
[45] Date of Patent: Dec. 2, 1997

[54] METHOD OF USING TRIARYL-ETHYLENE DERIVATIVES IN THE TREATMENT AND PREVENTION OF OSTEOPOROSIS

[75] Inventor: Alan J. Bitonti, Maineville, Ohio

[73] Assignee: Hoechst Marion Roussel, Inc., Cincinnati, Ohio

[21] Appl. No.: 662,092

[22] Filed: Jun. 12, 1996

Related U.S. Application Data

[60] Division of Ser. No. 531,885, Oct. 11, 1995, which is a continuation-in-part of Ser. No. 346,111, Nov. 29, 1994, abandoned.

[51] Int. Cl.⁶ .................................................. A61K 31/135
[52] U.S. Cl. ................. 514/648; 514/231.8; 514/235.5; 514/235.8; 514/237.8; 514/252; 514/255; 514/316; 514/326; 514/331; 514/408; 514/472
[58] Field of Search ............................ 514/231.8, 235.5, 514/239.8, 237.8, 252, 255, 316, 326, 331, 408, 422, 648

[56] References Cited

U.S. PATENT DOCUMENTS

| | | | |
|---|---|---|---|
| 2,914,563 | 11/1959 | Allen et al. | 564/324 |
| 3,247,252 | 4/1966 | Palopoli et al. | 564/326 |
| 4,001,229 | 1/1977 | Kreighbaum | 544/159 |
| 4,623,660 | 11/1986 | Richardson et al. | 514/514 |
| 4,729,999 | 3/1988 | Young | 514/227 |
| 4,894,373 | 1/1990 | Young | 514/239.2 |
| 4,970,237 | 11/1990 | Jensel et al. | 514/615 |
| 5,525,633 | 6/1996 | Mathews et al. | 514/648 |

FOREIGN PATENT DOCUMENTS

| | | |
|---|---|---|
| 0002097 | 8/1978 | European Pat. Off. . |
| 1013907 | 12/1965 | United Kingdom . |
| 1099093 | 1/1968 | United Kingdom . |
| 1128379 | 9/1968 | United Kingdom . |

OTHER PUBLICATIONS

Murphy, et al., Biochemical and Biophysical Research Communications, vol. 100 (3):1353–1360 (Jun. 16, 1981).
Murphy, et al., J. of Clinical Endocrinology and Metabolism, vol. 57 (2):373–379 (1983).
Clark, et al., Pharm. Ther, vol. 15:467–519 (1982).
Legha, et al., Cancer Treatment Reviews, 3:205–216 (1976).
Murphy, Leigh C. et al., *Rational Basis for Chemotheraphy* (1993) Proceedings of the UCLA Sym. at Keystone Colorado Apr. 18–23, 1982, pp. 195–210.
*Proceedings 85th annual Meeting American Association for Cancer Research*, Apr. 10–13, 1994 vol. 35, Mar. 1994.
Watts et al, *Journal of Biological Chemistry*, vol. 250, No. 7 pp. 4223–4229 (1994).
Palopoli et al, *J. Med. Chem.* vol. 10:84–86 (Jan. 1967).
Young Robert L., et al. *Int. J. Fertil.*, vol. 36, No. 3 May 1991 pp. 167–171.
Derwent Publication, AN 95–027627 JP A,06 312 930, 8 Nov. 1994.

*Primary Examiner*—Richard L. Raymond
*Attorney, Agent, or Firm*—David M. Stemerick

[57] ABSTRACT

The present invention relates to a method of using triaryl-ethylene derivatives in the treatment or prevention bone tissue loss or osteoporosis.

16 Claims, No Drawings

METHOD OF USING TRIARYL-ETHYLENE DERIVATIVES IN THE TREATMENT AND PREVENTION OF OSTEOPOROSIS

This application is a division of application Ser. No. 08/531,885, filed Oct. 11, 1995, which is a continuation-in-part of application Ser. No. 08/346,111, filed Nov. 29, 1994, now abandoned, which are herein incorporated by reference.

BACKGROUND OF THE INVENTION

The present invention relates to a method of using triaryl-ethylene derivatives in the treatment or prevention osteoporosis or bone tissue loss. Osteoporosis is a significant problem for the developed nations. The term osteoporosis is often used to describe different clinical situations. Osteoporosis was first used to describe the syndrome in which post-menopausal women tended to suffer vertebral fractures. F. Albright et al., *J. Am. Med. Assoc.* 116, 2465–2474 (1941). To avoid ambiguity, the terms bone tissue loss or osteopenia are used to describe the clinical situation in which loss of bone mass or density has occurred in the absence of a fracture.

Osteoporosis is most commonly associated with post-menoapuse and age related bone tissue loss. Osteoporosis or bone tissue loss can also occur secondarily to various drugs and diseases, including: corticosteroids, anticonvulsants, alcohol, malabsorption syndromes, primary biliary cirrhosis, myeloma, thalassemia, thyrotoxicosis, Cushing's syndrome, Turner's syndrome, and primary hyperparathyroidism.

SUMMARY OF THE INVENTION

The present invention relates to a method of using triaryl-ethylene derivatives in the treatment or prevention bone tissue loss or osteoporosis.

The present invention provides a method of treating or preventing bone tissue loss or osteoporosis in a patient, comprising administering an effective antiosteoporosis amount of a compound of Formula I:

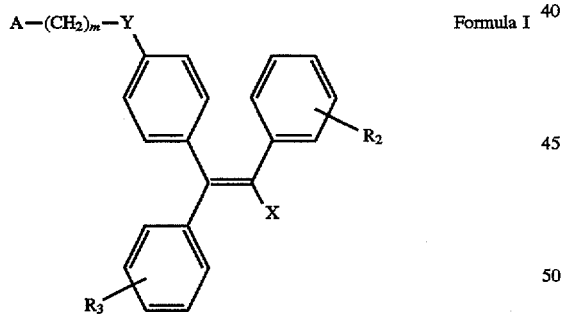

Formula I wherein

A is a radical of the formula

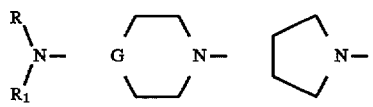

wherein

R and $R_1$ are each independently hydrogen or $C_1$–$C_4$ alkyl; and

G is HN, $H_3$CN, $CH_2$, or O;

m is an integer from 4 to 12;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_p$A$_1$ in which $A_1$ is a radical of the formula

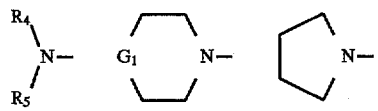

wherein $R_4$ and $R_5$ are each independently hydrogen or $C_1$–$C_4$ alkyl;

$G_1$ is HN, $H_3$CN, $CH_2$, or O; and p is an integer from 4 to 12;

X is chloro or bromo;

Y is O or NH;

or a pharmaceutically acceptable salt thereof.

In addition, the present invention provides a method of treating or preventing bone tissue loss or osteoporosis in a patient, comprising administering an effective antiosteoporosis amount of a compound of Formula II:

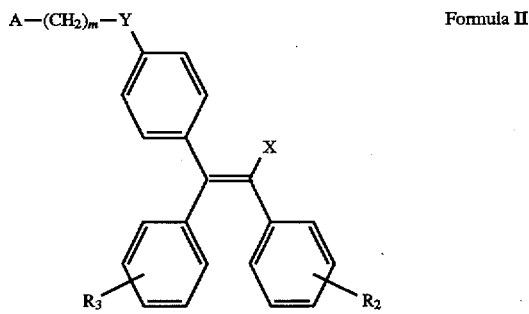

Formula II wherein

A is a radical of the formula

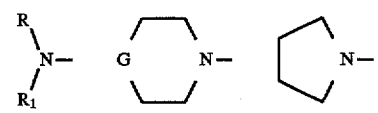

wherein

R and $R_1$ are each independently hydrogen or $C_1$–$C_4$ alkyl; and

G is HN, $H_3$CN, $CH_2$, or O;

m is an integer from 4 to 12;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_p$A$_1$ in which $A_1$ is a radical of the formula

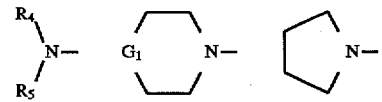

wherein $R_4$ and $R_5$ are each independently hydrogen or $C_1$–$C_4$ alkyl;

$G_1$ is HN, $H_3$CN, $CH_2$, or O; and p is an integer from 4 to 12;

X is chloro or bromo;

Y is O or NH;

or a pharmaceutically acceptable salt thereof.

In addition, the present invention provides a method of treating or preventing bone tissue loss or osteoporosis in a patient, comprising administering an effective antiosteoporosis amount of a compound of the Formula III:

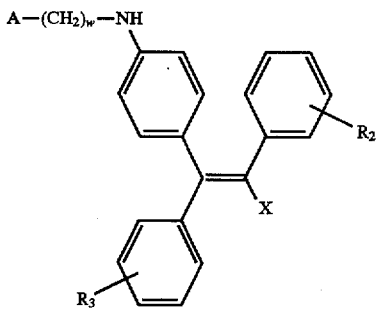
Formula III wherein

A is a radical of the formula

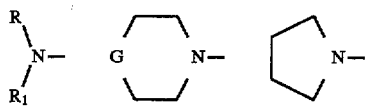

wherein

R and $R_1$ are each independently hydrogen or $C_1$–$C_4$ alkyl; and

G is HN, $H_3$CN, $CH_2$, or O;

w is an integer from 2 to 3;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_z$A$_1$ in which $A_1$ is a radical of the formula

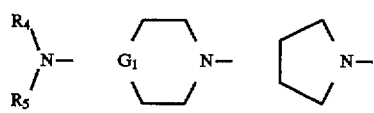

wherein

Y is —NH—

$R_4$ and $R_5$ are each independently hydrogen or $C_1$–$C_4$ alkyl;

$G_1$ is HN, $H_3$CN, $CH_2$, or O; and z is an integer from 2 to 3;

X is chloro or bromo;

or a pharmaceutically acceptable salt thereof.

In addition, the present invention provides a method of treating or preventing bone tissue loss or osteoporosis in a patient, comprising administering an effective antiosteoporosis amount of a compound of the Formula IV:

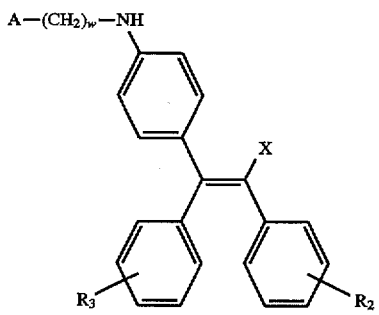
Formula IV wherein

A is a radical of the formula

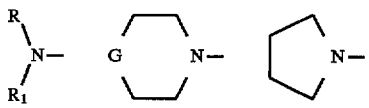

wherein

R and $R_1$ are each independently hydrogen or $C_1$–$C_4$ alkyl; and

G is HN, $H_3$CN, $CH_2$, or O;

w is an integer from 2 to 3;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_z$A$_1$ in which $A_1$ is a radical of the formula

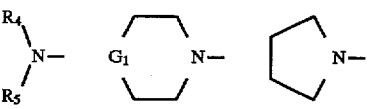

wherein

Y is —NH—

$R_4$ and $R_5$ are each independently hydrogen or $C_1$–$C_4$ alkyl;

$G_1$ is HN, $H_3$CN, $CH_2$, or O; and z is an integer from 2 to 3;

X is chloro or bromo;

or a pharmaceutically acceptable salt thereof.

In addition the present invention provides a pharmaceutical composition for oral administration comprising an effective antiosteoporosis amount of a compound of Formula III or Formula IV in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated, straight or branched chain, hydrocarbon radical of one to four carbon atoms and includes methyl, ethyl, propyl, isopropyl, n-butyl, isobutyl, t-butyl, and the like.

As used herein, the designation "halogen" refers to a bond for which the stereochemistry is not designated.

As used herein, the term "halogen" refers to a fluorine, chlorine, bromine, or iodine atom.

As used herein, the term "$C_1$–$C_4$ alkoxy" refers to a $C_1$–$C_4$ alkyl bearing an oxy group and includes methoxy, ethoxy, n-propoxy, n-butoxy, iso-propoxy, iso-butoxy, t-butoxy, and the like.

As used herein, the term "hydroxy" or "hydroxy group" refers to a —OH radical.

As used herein, the term "$(CH_2)_n$" refers to a straight chain alkylene radical of from 2 carbon atoms to 12 carbon atoms for example; ethyl, propyl, butyl, pentyl, hexyl, heptyl, octyl, nonyl, decyl, undecyl, and dodecyl.

As used herein, the term "$(CH_2)_m$" refers to a straight chain alkylene radical of from 4 carbon atoms to 12 carbon atoms for example; butyl, pentyl, hexyl, heptyl, octyl, nonyl, decyl, undecyl, and dodecyl.

As used herein, the term "$(CH_2)_p$" refers to a straight chain alkylene radical of from 4 carbon atoms to 12 carbon atoms for example; butyl, pentyl, hexyl, heptyl, octyl, nonyl, decyl, undecyl, and dodecyl.

As used herein, the term "$(CH_2)_w$" refers to a straight chain alkylene radical of from 2 carbon atoms to 3 carbon atoms for example; ethyl and propyl.

As used herein, the term "$(CH_2)_z$" refers to a straight chain alkylene radical of from 2 carbon atoms to 3 carbon atoms for example; ethyl and propyl.

As used herein, the term "pharmaceutically acceptable addition salt refers to either an acid addition salt or a basic addition salt.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethane sulfonic acid. Either the mono- or di-acid salts may be formed, and such salts may exist in either a hydrated or substantially anhydrous form.

Compounds of Formula I, Formula II, Formula III, and Formula IV exist as geometric isomers. Any reference in this application to one of the compounds represented by Formula I, Formula II, Formula III, and Formula IV is meant to encompass each of the specific geometric isomers. The specific geometric isomers can be separated and recovered by techniques known in the art such as chromatography on silica gel, chromatography on a reverse-phase adsorbent, or fractional recrystallization. As is well known by one of ordinary skill in the art the Cahn-Ingold-Prelog designation of (E)- and (Z)- for isomers of compounds of Formula I, Formula II, Formula III, and Formula IV depends on the nature of Y, X, m, w, p, z, A, $A_1$, $R_2$, and $R_3$. As is apparent to one of ordinary skill in the art compounds of Formula I or II in which the substituent $R_3$ is —$Y(CH_2)_pA_1$ and p=n and A=$A_1$ do not exist as geometrical isomers. Similarly, for compounds of Formula III or IV in which the substituent $R_3$ is —$NH(CH_2)_zA_1$ and w=z and A=$A_1$ do not exist as geometrical isomers.

As is apparent to one of ordinary skill in the art, the compounds of Formula I and Formula II include compounds wherein m is an integer from 4 to 12. The compounds of Formula III and Formula IV include compounds wherein w is an integer from 2 to 3. Therefore, it is understood that a description of the preparation of compounds that differ from the compounds of Formula I and II in that $(CH_2)_m$ is instead $(CH_2)_n$ wherein n is defined as an integer from 2 to 12 comprehends and provides a description of the preparation of the compounds of Formula I, Formula II, Formula III, and Formula IV.

Illustrative Examples of compounds encompassed by the present invention include:

(E)-1-[4-(4-Diethylaminobutoxy)phenyl]-1,2-diphenyl-2-chloro-ethylene;

(Z)-1-[4-(4-Diethylaminobutoxy)phenyl]-1,2-diphenyl-2-chloro-ethylene;

(E)-1-[4-(5-Diethylaminopentoxy)phenyl]-1,2-diphenyl-2-chloro-ethylene;

(Z)-1-[4-(5-Diethylaminopentoxy)phenyl]-1,2-diphenyl-2-chloro-ethylene;

(E)-1-[4-(6-Diethylaminohexoxy)phenyl]-1,2-diphenyl-2-chloro-ethylene;

(Z)-1-[4-(6-Diethylaminohexoxy)phenyl]-1,2-diphenyl-2-chloro-ethylene;

(E)-1-[4-(7-Diethylaminoheptoxy)phenyl]-1,2-diphenyl-2-chloro-ethylene;

(Z)-1-[4-(7-Diethylaminoheptoxy)phenyl]-1,2-diphenyl-2-chloro-ethylene;

(E)-1-[4-(8-Diethylaminooctoxy)phenyl]-1,2-diphenyl-2-chloro-ethylene;

(Z)-1-[4-(8-Diethylaminooctoxy)phenyl]-1,2-diphenyl-2-chloro-ethylene;

(E)-1-[4-(9-Diethylaminononoxy)phenyl]-1,2-diphenyl-2-chloro-ethylene;

(Z)-1-[4-(9-Diethylaminononoxy)phenyl]-1,2-diphenyl-2-chloro-ethylene;

(E)-1-[4-(10-Diethylaminodecoxy)phenyl]-1,2-diphenyl-2-chloro-ethylene;

(Z)-1-[4-(10-Diethylaminodecoxy)phenyl]-1,2-diphenyl-2-chloro-ethylene;

(E)-1-[4-(11-Diethylaminoundecoxy)phenyl]-1,2-diphenyl-2-chloro-ethylene;

(Z)-1-[4-(11-Diethylaminoundecoxy)phenyl]-1,2-diphenyl-2-chloro-ethylene;

(E)-1-[4-(12-Diethylaminododecoxy)phenyl]-1,2-diphenyl-2-chloro-ethylene;

(Z)-1-[4-(12-Diethylaminododecoxy)phenyl]-1,2-diphenyl-2-chloro-ethylene;

(E)-1-[4-(2-Diethylaminoethylamino)phenyl]-1,2-diphenyl-2-chloro-ethylene;

(Z)-1-[4-(2-Diethylaminoethylamino)phenyl]-1,2-diphenyl-2-chloro-ethylene;

(E)-1-[4-(3-Diethylaminopropylamino)phenyl]-1,2-diphenyl-2-chloro-ethylene;

(Z)-1-[4-(3-Diethylaminopropylamino)phenyl]-1,2-diphenyl-2-chloro-ethylene;

(E)-1-[4-(4-Diethylaminobutylamino)phenyl]-1,2-diphenyl-2-chloro-ethylene;

(Z)-1-[4-(4-Diethylaminobutylamino)phenyl]-1,2-diphenyl-2-chloro-ethylene;

(E)-1-[4-(4-Diethylaminobutoxy)phenyl]-1,2-diphenyl-2-bromo-ethylene;

(Z)-1-[4-(4-Diethylaminobutoxy)phenyl]-1,2-diphenyl-2-bromo-ethylene;

(E)-1-[4-(2-Diethylaminoethylamino)phenyl]-1,2-diphenyl-2-bromo-ethylene;

(Z)-1-[4-(2-Diethylaminoethylamino)phenyl]-1,2-diphenyl-2-bromo-ethylene;

(E)-1-[4-(3-Diethylaminopropylamino)phenyl]-1,2-diphenyl-2-bromo-ethylene;

(Z)-1-[4-(3-Diethylaminopropylamino)phenyl]-1,2-diphenyl-2-bromo-ethylene;

(E)-1-[4-(4-Diethylaminobutylamino)phenyl]-1,2-diphenyl-2-bromo-ethylene (Z)-1-[4-(4-Diethylaminobutylamino)phenyl]-1,2-diphenyl-2-bromo-ethylene;

1,1-Bis-[4-(4-diethylaminobutoxy)phenyl]-2-phenyl-2-chloro-ethylene;

(E)-1-[4-(4-Diethylaminobutoxy)phenyl]-1-(4-hydroxy)phenyl-2-phenyl-2-chloro-ethylene;

(Z)-1-[4-(4-Diethylaminobutoxy)phenyl]-1-(4-hydroxy)phenyl-2-phenyl-2-chloro-ethylene;

(E)-1-[4-(4-Diethylaminobutoxy)phenyl]-1-(3-hydroxy)phenyl-2-phenyl-2-chloro-ethylene;

(Z)-1-[4-(4-Diethylaminobutoxy)phenyl]-1-(3-hydroxy)phenyl-2-phenyl-2-chloro-ethylene;

(E)-1-[4-(4-Diethylaminobutoxy)phenyl]-1-phenyl-2-(4-hydroxy)phenyl-2-chloro-ethylene;

(Z)-1-[4-(4-Diethylaminobutoxy)phenyl]-1-phenyl-2-(4-hydroxy)phenyl-2-chloro-ethylene;

(E)-1-[4-(4-Diethylaminobutoxy)phenyl]-1-phenyl-2-(3-hydroxy)phenyl-2-chloro-ethylene;

(Z)-1-[4-(4-Diethylaminobutoxy)phenyl]-1-phenyl-2-(3-hydroxy)phenyl-2-chloro-ethylene;

(E)-1-[4-(4-Ethylaminobutoxy)phenyl]-1,2-diphenyl-2-chloro-ethylene;

(Z)-1-[4-(4-Ethylaminobutoxy)phenyl]-1,2-diphenyl-2-chloro-ethylene;

(E)-1-[4-(4-Methylaminobutoxy)phenyl]-1,2-diphenyl-2-chloro-ethylene;

(Z)-1-[4-(4-Methylaminobutoxy)phenyl]-1,2-diphenyl-2-chloro-ethylene;

(E)-1-[4-(4-Propylaminobutoxy)phenyl]-1,2-diphenyl-2-chloro-ethylene;

(Z)-1-[4-(4-Propylaminobutoxy)phenyl]-1,2-diphenyl-2-chloro-ethylene;

(E)-1-[4-(4-Dimethylaminobutoxy)phenyl]-1-(4-hydroxy)phenyl-2-phenyl-2-chloro-ethylene;

(Z)-1-[4-(4-Dimethylaminobutoxy)phenyl]-1-(4-hydroxy)phenyl-2-phenyl-2-chloro-ethylene;

(E)-1-[4-(4-Dipropylaminobutoxy)phenyl]-1-(4-hydroxy)phenyl-2-phenyl-2-chloro-ethylene;

(Z)-1-[4-(4-Dipropylaminobutoxy)phenyl]-1-(4-hydroxy)phenyl-2-phenyl-2-chloro-ethylene;

(E)-1-[4-(4-Dimethylaminobutoxy)phenyl]-1,2-phenyl-2-phenyl-2-chloro-ethylene;

(Z)-1-[4-(4-Dimethylaminobutoxy)phenyl]-1,2-diphenyl-2-phenyl-2-chloro-ethylene;

(E)-1-[4-(4-Dipropylaminobutoxy)phenyl]-1,2-diphenyl-2-phenyl-2-chloro-ethylene;

(Z)-1-[4-(4-Dipropylaminobutoxy)phenyl]-1,2-diphenyl-2-phenyl-2-chloro-ethylene;

(E)-1-[4-(4-(Piperidin-1-yl)-butoxy)phenyl]-1,2-diphenyl-2-chloro-ethylene;

(Z)-1-[4-(4-(Piperidin-1-yl)-butoxy)phenyl]-1,2-diphenyl-2-chloro-ethylene;

(E)-1-[4-[4-(Piperazin-1-yl)-butoxy)phenyl]-1,2-diphenyl-2-chloro-ethylene;

(Z)-1-[4-[4-(Piperazin-1-yl)-butoxy)phenyl]-1,2-diphenyl-2-chloro-ethylene;

(E)-1-[4-[4-(4-Methylpiperazin-1-yl)-butoxy)phenyl]-1,2-diphenyl-2-chloro-ethylene;

(Z)-1-[4-[4-(4-Methylpiperazin-1-yl)-butoxy)phenyl]-1,2-diphenyl-2-chloro-ethylene;

(E)-1-[4-(4-(Morpholin-1-yl)-butoxy)phenyl]-1,2-diphenyl-2-chloro-ethylene;

(Z)-1-[4-(4-(Morpholin-1-yl)-butoxy)phenyl]-1,2-diphenyl-2-chloro-ethylene;

(E)-1-[4-(4-(Pyrrolidin-1-yl)-butoxy)phenyl]-1,2-diphenyl-2-chloro-ethylene;

(Z)-1-[4-(4-(Pyrrolidin-1-yl)-butoxy)phenyl]-1,2-diphenyl-2-chloro-ethylene.

The compounds of Formula I and II in which Y is O can be prepared as described in Scheme A. All substituents, unless otherwise indicated, are previously defined. The reagents and starting materials are readily available to one of ordinary skill in the art.

SCHEME A

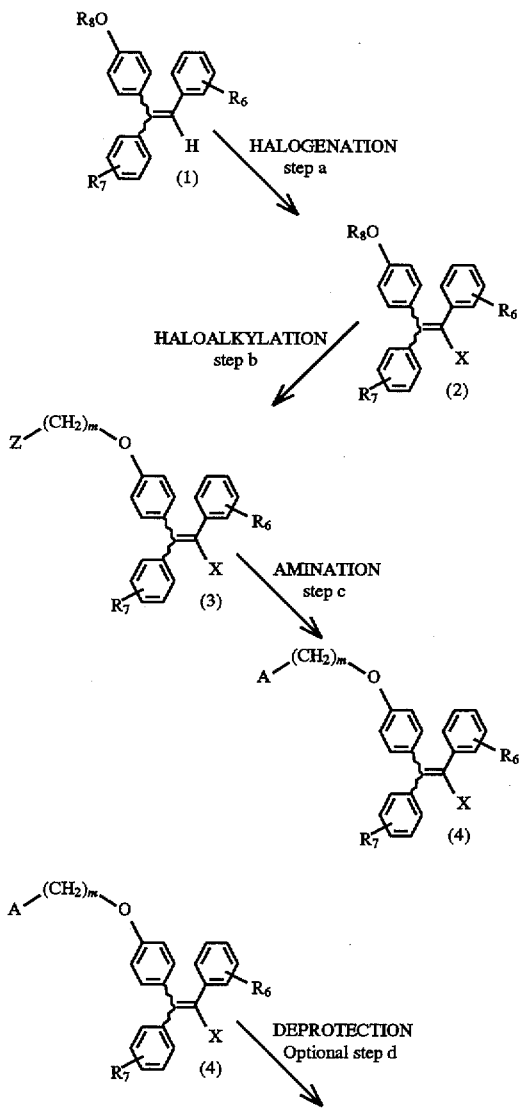

-continued
SCHEME A

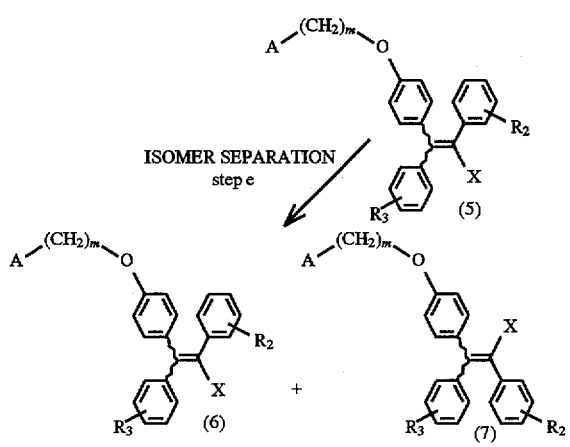

In Scheme A, step a, an appropriate triaryl-ethylene of structure 1 is chlorinated or brominated to give a halotriaryl-ethylene of structure 2.

An appropriate triaryl-ethylene of the structure 1 is one in which $R_8$ is hydrogen, an ω-haloalkyl group, $Z(CH_2)_m$— in which Z may be a chlorine atom, a bromine atom, or a iodine atom and m is as desired in the final product, or a suitable hydroxy protecting group; $R_6$ is as defined for $R_2$, or $R_6$ is a suitably protected hydroxy which after deprotection provide compounds of Formula I and Formula II in which $R_2$ is a hydroxy group; and $R_7$ is as defined for $R_3$, or $R_7$ is a suitably protected hydroxy which after deprotection provide compounds of Formula I and Formula II in which $R_3$ is a hydroxy group, or provides an intermediate for the preparation of a compound of Formula I and Formula II in which $R_3$ is —$O(CH_2)_pA_1$ wherein p=m and A=$A_1$; or $R_7$ is a suitably protected hydroxy which allows for removal in a sequential manner providing an intermediate for the preparation of compounds of Formula I and Formula II in which $R_3$ is —$O(CH_2)_pA_1$ wherein p≠m and either A=$A_1$ or A≠$A_1$, or in which $R_3$ is —$O(CH_2)_pA_1$ wherein p=m and A≠$A_1$. The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

For example, an appropriate triaryl-ethylene of structure 1 is contacted with a molar excess of chlorine, bromine, N-chlorosuccinimide, or N-bromosuccinimide in a suitable solvent, such as chloroform, chlorobenzene, or dichloromethane. The reaction is carried out at temperatures from ambient temperature to the reflux temperature of the solvent. After stirring for from 1–72 hours the product can be isolated and purified by techniques well known in the art. For example, the reaction mixture can be concentrated in vacuo and the product purified by chromatography on silica gel eluting with a suitable organic solvent. The material obtained can be further purified, if desired, by recrystallization from a suitable organic solvent to give a halo-triaryl-ethylene of structure 2.

As is appreciated by one of ordinary skill in the art, when a halo-triaryl-ethylene of structure 2 is derived from a triaryl-ethylene of structure 1 in which $R_8$ is a suitable hydroxy protecting group, the protecting group is removed before step b can be carried out. When a halo-triaryl-ethylene of structure 2 is derived from a triaryl-ethylene of structure 1 in which $R_8$ is a suitable protecting group and $R_7$ is a suitably protected hydroxy either the protecting groups are removed before step b is carried out or they are removed in a sequential manner. When the protecting groups are removed in a sequential manner intermediates are provided for the preparation of compounds of Formula I and Formula II in which $R_3$ is —$O(CH_2)_pA_1$ wherein p≠m and either A=$A_1$ or A≠$A_1$ and in which $R_3$ is —$O(CH_2)_pA_1$ wherein p=m and A≠$A_1$.

In Scheme A, step b, a halo-triaryl-ethylene of structure 2 is contacted with an appropriate dihaloalkane to form a ω-haloalkoxy-triaryl-ethylene of structure 3.

An appropriate dihaloalkane, $Z(CH_2)_mZ_1$, is one in which Z and $Z_1$ each may be independently a chlorine atom, a bromine atom, or a iodine atom and m is as desired in the final product of Formula I and Formula II.

For example, a halo-triaryl-ethylene of structure 2 is contacted with a 1.1 to 10 fold molar excess of an appropriate dihaloalkane. The reaction is carried out in the presence of a suitable base, such as sodium ethoxide, sodium methoxide, potassium hydroxide, sodium hydroxide, and sodium carbonate. The reaction is carried out in a solvent, such as ethanol, methanol, tetrahydrofuran, acetonitrile, dimethylformamide, or dimethyl sulfoxide. The reaction is carried out at temperatures of from 0° C. to the refluxing temperature of the solvent. For compounds of structure 2 in which $R_8$ is hydrogen and $R_7$ is a hydroxy group the use 1.1 molar equivalents of an appropriate dihaloalkane and a suitable base allows for the preparation of a compound of Formula I and Formula II in which $R_7$ is a hydroxy group. For compounds of structure 2 in which $R_8$ is hydrogen and $R_7$ is a hydroxy group the use of from 2 to 10 molar equivalents of an appropriate dihaloalkane and a suitable base gives an bis-ω-haloalkoxy-triaryl-ethylene which is an intermediate in the production of a compound of Formula I and Formula II in which $R_3$ is —$O(CH_2)_pA_1$ wherein p=m and A=$A_1$. A ω-haloalkoxy-triaryl-ethylene of structure 3 may be isolated from the reaction zone by evaporation and extraction and may be purified by methods well known in the art, such as chromatography and recrystallization.

In Scheme A, step c, ω-haloalkoxy-triaryl-ethylene of structure 3 is contacted with an appropriate amine, $HNRR_1$, in which R and $R_1$ are as defined above, morpholine, piperidine, piperazine, 4-methylpiperazine, or pyrrolidine to give ω-aminoalkoxy-triaryl-ethylene of structure 4.

For example, ω-haloalkoxy-triaryl-ethylene of structure 2 is contacted with a large molar excess of an appropriate amine in a solvent, such as ethanol, methanol, water, ethanol/water mixtures, or methanol/water mixtures. A large molar excess of amine is used so that the amine can also acts as a base to take up the acid liberated in the reaction. The reaction may be carried out in the presence of a suitable catalyst, such as potassium iodide. The reaction vessel may be sealed to prevent the escape of volatile amines. The reaction mixture is heated to temperatures of from 40° C. to 100° C. For compounds of structure 3 in which $R_7$ is a ω-haloalkoxy group the use of an additional portion of an appropriate amine gives a bis-ω-aminoalkoxy-triaryl-ethylene which is a compound of Formula I and Formula II in which $R_3$ is —$O(CH_2)_pA_1$ wherein p=m and A=$A_1$. The product can be isolated and purified by techniques well known in the art. For example, the reaction mixture can be concentrated in vacuo and the product purified by techniques well known in the art, such as salt formation, chromatography eluting with a suitable solvent, or recrystallization from a suitable organic solvent.

In Scheme A, step a, may be carried out before or after steps b and c are carried out.

In Scheme A, optional step d, for a ω-aminoalkoxy-triaryl-ethylene of structure 4 in which $R_6$ or $R_7$ is a protected hydroxy group may be deprotected to provide ω-aminoalkoxy-triaryl-ethylene of structure 5 in which either, $R_2$ or $R_3$, or $R_2$ and $R_3$, are hydroxy as desired in the final product of Formula I and Formula II. As is appreciated by one skilled in the art the compounds of Formula I and Formula II in which $R_3$ is hydroxy can be, by sequentially performing the steps of Scheme A, used as intermediates for preparing compounds of Formula I and Formula II in which $R_3$ is —O(CH$_2$)$_p$A$_1$ wherein p≠m and either A=A$_1$ or A≠A$_1$ or in which $R_3$ is —O(CH$_2$)$_p$A$_1$ wherein p=m and A≠A$_1$.

The selection, use, removal, and sequential removal of suitable hydroxy protecting groups is well known and appreciated in the art and described in *Protecting Groups in Organic Synthesis* by T. Greene.

In Scheme A, step e, the isomers of a ω-aminoalkoxy-triaryl-ethylene of structure 4 or 5 can be separated to give a (E)-ω-aminoalkoxy-triaryl-ethylene of structure 4 or 5 and the (Z)-ω-aminoalkoxy-triaryl-ethylene of structure 4 or 5.

For example, the isomers of compounds of structure 5 can be separated and purified by high-performance liquid chromatography or recrystallization of salt to give a (E)-ω-aminoalkoxy-triaryl-ethylene and a (Z)-ω-aminoalkoxy-triaryl-ethylene.

Pharmaceutically acceptable salts of a (E)-ω-aminoalkoxy-triaryl-ethylene of or of a (Z)-ω-aminoalkoxy-triaryl-ethylene can be formed in an additional step as is well known and practiced in the art.

The following examples present typical syntheses as described in Scheme A. These examples are understood to be illustrative only and are not intended to limit the scope of the invention in any way. As used in the following examples, the following terms have the meanings indicated: "kg" refers to kilograms, "g" refers to grams, "mg" refers to milligrams, "mmol" refers to millimoles, "mol" refers to moles, "mL" refers to milliliters, "L" refers to liters, "°C." refers to degrees Celsius, "$R_f$" refers to retention factor, "mp" refers to melting point, "HPLC" refers to high performance liquid chromatography.

EXAMPLE 1

(E and Z)-1-[(4-Hydroxy)phenyl]-1,2-diphenyl-2-chloro-ethylene

Combine (E and Z)-1-[(4-hydroxy)phenyl]-1,2-diphenyl-ethylene [Cacchi et al, *Tet. Lets.* 25, 3137–3140 (1984)] (0.90 g, 3.31 mmol) and N-chlorosuccinimide (0.486 g, 3.64 mmol) in chloroform (20 mL). Heat to reflux and allow to stir at reflux for 48 hours. Evaporate in vacuo. Chromatograph on silica gel eluting with 20% ethyl acetate/hexane to give the title compound as a solid: mp; 127°–129° C.

EXAMPLE 2

(E and Z)-1-[4-(4-Chlorobutoxy)phenyl]-1,2-diphenyl-2-chloro-ethylene

Combine (E and Z)-1-[(4-hydroxy)phenyl]-1,2-diphenyl-2-chloro-ethylene (15.0 g, 49.0 mmol) and 4-bromo-1-chlorobutane (35 g, 200 mmol) in ethanol (250 mL). Add sodium methoxide (2.75 g, 50.0 mmol). Heat to reflux under an inert atmosphere. After 5 hours concentrate on a steam bath to obtain a residue. Partition the residue between diethyl ether and 10% sodium hydroxide. Separate the layers and dry the organic layer over MgSO$_4$, filter, and evaporate in vacuo to give the title compound which is taken on to the next step without further purification.

EXAMPLE 3

(E and Z)-1-[4-(4-Diethylaminobutoxy)phenyl]-1,2-diphenyl-2-chloro-ethylene

Combine (E and Z)-1-[4-(4-chlorobutoxy)phenyl]-1,2-diphenyl-2-chloro-ethylene (19.0 g, 47.8 mmol), diethylamine (20 mL, 193 mmol), and ethanol (100 mL). Seal in a reaction vessel and heat to 80° C. for 48 hours. Cool to ambient temperature and carefully open the pressure vessel. Concentrate in vacuo to obtain a residue. Dissolve the residue in butanone and add citric acid (9.0 g, 47 mmol). Filter to give a mixture of the isomers as their citric acid salts. Dissolve (E and Z)-1-[4-(4-diethylaminobutoxy)phenyl]-1,2-diphenyl-2-chloro-ethylene citric acid salts (1.5 g) in 1/1 acetonitrile/water and adjust the pH to 9 with 2M aqueous sodium hydroxide. Extract with chloroform and evaporate to give a mixture of the isomers as a residue. Separate the isomers by HPLC, 90 mg per injection, using a Waters and Associates μPorasil column (19 mm by 300 mm), eluting with 80/20/0.2 chloroform/hexane/triethylamine at 15 mL/minute to give (Z)-1-[4-(4-diethylaminobutoxy)phenyl]-1,2-diphenyl-2-chloro-ethylene and (E)-1-[4-(4-diethylaminobutoxy)phenyl]-1,2-diphenyl-2-chloro-ethylene.

EXAMPLE 3.1

(E and Z)-1-[4-(4-Diethylaminobutoxy)phenyl]-1,2-diphenyl-2-chloro-ethylene hydrochloride salt Combine 4-hydroxybenzophenone (347 g, 1.75 mol) and methanol (3.5 L). Heat to 50° C. and add a solution of sodium ethanolate in ethanol (718 mL, 21% by weight, 1.92 mol) over 20 minutes. Heat to reflux and add 1-bromo-4-chlorobutane (600 g, 3.5 mol) over 30 minutes. After 18 hours, cool the reaction mixture and evaporate in vacuo to obtain a residue.

Add ethyl acetate (5 L) to give a solid. Filter and extract the filtrate with aqueous 10% sodium hydroxide solution and aqueous saturated sodium chloride solution. Dry the organic layer over MgSO$_4$, filter, and evaporate in vacuo to give 4-(4-chlorobutoxy)benzophenone.

Combine 4-(4-chlorobutoxy)benzophenone (740 g, 1.59 mol), diethylamine (3.7 L), and potassium iodide (50 g) in water (3.7 L). Heat to reflux. After 19 hours, evaporate the reaction mixture in vacuo to give an aqueous residue. Extract two times with ethyl acetate. Extract the combined organic layers with aqueous 10% hydrochloric acid solution and separate the acidic aqueous layer. Combine the acidic aqueous layer and ethyl acetate. Slowly add aqueous 10% sodium hydroxide solution until the pH of the aqueous layer is about 9. Separate the organic layer, extract twice with water and then aqueous saturated sodium chloride solution. Dry the organic layer over MgSO$_4$, filter, and evaporate in vacuo to give 4-(4-diethylaminobutoxy)benzophenone.

Combine 4-(4-diethylaminobutoxy)benzophenone (400 g, 1.13 mol) and tetrahydrofuran (4 L). Add a solution of benzylmagnesium chloride (1.1 L, 2.0M in tetrahydrofuran, 2.2 mol) over about 30 minutes. After 1 hour, heat to reflux. After 2 hours, cool to ambient temperature. Cautiously add aqueous saturated ammonium chloride solution (4 L) and a precipitate forms. Filter the reaction mixture, rinse with tetrahydrofuran, and extract the filtrate with aqueous saturated sodium chloride solution. Dry the organic layer over MgSO$_4$, filter, and evaporate in vacuo to give a residue. Combine the residue and butanone. Add citric acid (250 g, 1.3 mol) and cool to give a solid. Collect the solid by filtration rinse with diethyl ether and dry to give 1-(4-diethylaminobutoxy)phenyl-1,2-diphenyl ethanol citrate salt.

Combine 1-(4-diethylaminobutoxy)phenyl-1,2-diphenyl ethanol citrate salt (550 g, 0.90 mol)and water (2.2 L). Heat to 75° C. After a solution is obtained, cool to 10° C. Adjust the pH to about 10.0 using aqueous 25% sodium hydroxide. Extract three times with diethyl ether. Combine the organic layers and extract with water and aqueous saturated sodium chloride solution. Dry the organic layer over $MgSO_4$, filter, and evaporate in vacuo to give a residue. Combine the residue and methanol (1 L) and aqueous 3M hydrochloric acid solution (2.2 L). Heat to reflux. After 2 hours, distill to remove most of the methanol and cool the resulting reaction mixture to ambient temperature. After 18 hours, adjusting the pH to about 10 using aqueous 25% sodium hydroxide solution while maintaining the temperature of the reaction mixture at 20° C. Extract the reaction mixture three times with diethyl ether. Combine the organic layers, extract with water and aqueous saturated sodium chloride solution. Dry the organic layers over $MgSO_4$, filter, and evaporate in vacuo to give a residue. Combine the residue with methanol (3.2 L) and add a methanolic hydrochloric acid solution until wet Congo Red paper gives a positive test for excess acid. Evaporate in vacuo to give a residue. Two times, add chloroform and evaporate in vacuo to give (E and Z)-1-(4-diethylaminobutoxy)phenyl-1,2-diphenyl ethylene hydrochloric acid salt.

Combine (E and Z)-1-(4-diethylaminobutoxy)phenyl-1,2-diphenyl ethylene hydrochloric acid salt (449 g, 0.9 mol) and chloroform (1.6 L). Add a cold (5° C.) solution of chlorine (68.4 g, 0.96 mol) in carbon tetrachloride (3.18 kg) over about 20 minutes while maintaining the temperature of the reaction mixture below 20° C. After 18 hours, heat to reflux. After 2 hours, cool to ambient temperature and evaporate in vacuo to give the title compound.

EXAMPLE 3.2

(E and Z)-1-[4-(4-Diethylaminobutoxy)phenyl]-1,2-diphenyl-2-chloro-ethylene hydrochloride salt Combine 4-hydroxybenzophenone (8 kg, 57.6 mol), potassium carbonate (8 kg, 57.6 mol), and 1-bromo-4-chlorobutane (8.384 kg, 48.9 mol) in acetone (40 L). Heat to reflux. After 20 hours, cool the reaction mixture and filter. Rinse the filter cake with acetone and evaporate the filtrate in vacuo to obtain 4-(4-chlorobutoxy) benzophenone.

Combine 4-(4-chlorobutoxy)benzophenone (8.1 kg, 13.47 mol) and tetrahydrofuran (60 L). Add a solution of benzylmagnesium chloride (21 L, 1.67M in tetrahydrofuran, 35 mol) over about 2.5 hours. After 2 hours, cautiously add aqueous saturated ammonium chloride solution (9 L) over about 1 hour and a precipitate forms. Filter the reaction mixture, rinse with tetrahydrofuran, and extract the filtrate with aqueous saturated sodium chloride solution. Evaporate the separated organic layer in vacuo to give 1-(4-chlorobutoxy)phenyl-1,2-diphenyl ethanol.

Combine 1-(4-chlorobutoxy)phenyl-1,2-diphenyl ethanol (17.0 kg, 20.2 mol) and methanol (30 L). Add aqueous 3M hydrochloric acid solution (40 L). Heat to reflux. After 2 hours, remove most of the methanol by distillation and cool the aqueous reaction mixture. Extract with chloroform. Extract the organic layer with aqueous saturated sodium carbonate solution. Separate the organic layer and evaporate in vacuo to give (E and Z)-1-(4-chlorobutoxy)phenyl-1,2-diphenyl ethylene.

Combine (E and Z)-1-(4-chlorobutoxy)phenyl-1,2-diphenyl ethylene (20.2 mol) and chloroform (60 L). Add N-chlorosuccinimide (7 kg, 52.4 mol). Heat to reflux. After 18 hours, cool to ambient temperature and add water. Separate the organic layer and extract with aqueous saturated sodium carbonate solution. Separate the organic layer and evaporate in vacuo to give (E and Z)-1-(4-chlorobutoxy)phenyl-2-chloro-1,2-diphenyl ethylene.

Combine (E and Z)-1-(4-chlorobutoxy)phenyl-2-chloro-1,2-diphenyl ethylene (20.2 mol), diethylamine (25 L, 241.7 mol), and potassium iodide (3.5 kg, 21.1 mol) in water (15 L). Heat to reflux. After 18 hours, evaporate the reaction mixture in vacuo to give an aqueous residue. Extract two times with ethyl acetate. Evaporate the organic layer in vacuo to give a residue. Combine the residue and acetone (50 L). Add a solution of citric acid (8 kg) in acetone (40 L). Heat to form a solution and cool to give solid. Collect the solid by filtration, rinse with acetone, and dry to give (E and Z)-1-[4-(4-diethylaminobutoxy)phenyl]-1,2-diphenyl-2-chloro-ethylene citrate salt.

Combine (E and Z)-1-[4-(4-diethylaminobutoxy)phenyl]-1,2-diphenyl-2-chloro-ethylene citrate salt (15.1 kg, 24.1 mol), sodium hydroxide (3.0 kg, 75 mol), and water (20 L). Extract with ethyl acetate. Separate the organic layer and dry azeotropically at 78° C. Cool the organic layer to 15° C., add hydrochloric acid gas until an acidic solution is obtained. Evaporate in vacuo to obtain the title compound.

EXAMPLE 4

(E)-1-[4-(4-Diethylaminobutoxy)phenyl]-1,2-diphenyl-2-chloro-ethylene citrate salt

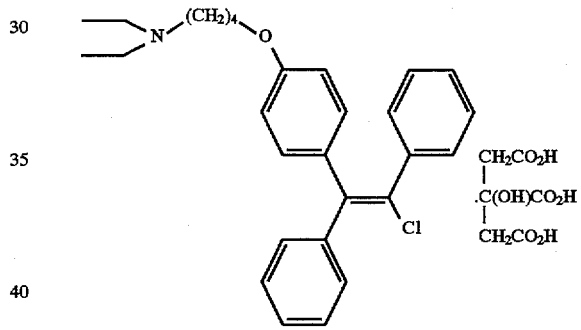

Combine citric acid (164.7 mg, 0.86 mmol) and ethanol (3 mL) and heat until the solid dissolves. Combine (E)-1-[4-(4-diethylaminobutoxy)phenyl]-1,2-diphenyl-2-chloro-ethylene (372.6 mg, 0.86 mmol) and warm ethanol (3 mL) and add with stirring to the citric acid solution prepared above. Cool to 4° C. and allow to stand for 18 hours. Filter to give the title compound as a solid: mp; 127°–130° C.

EXAMPLE 4.1

(E)-1-[4-(4-Diethylaminobutoxy)phenyl]-1,2-diphenyl-2-chloro-ethylene citrate salt Combine (E and Z)-1-[4-(4-diethylaminobutoxy)phenyl]-1,2-diphenyl-2-chloro-ethylene hydrochloride salt (0.45 mol) and tetrahydrofuran (2 L). Heat to reflux. After 1 hour, cool to ambient temperature to give a solid. Collect the solid by filtration, rinse with tetrahydrofuran, and dry. Combine the solid and tetrahydrofuran (420 mL) and heat to reflux. After 24 hours, filter the mixture while hot, rinse with tetrahydrofuran, and dry to give (E)-1-[4-(4-diethylaminobutoxy)phenyl]-1,2-diphenyl-2-chloro-ethylene hydrochloride salt: mp; 188°–190° C.

Combine (E)-1-[4-(4-diethylaminobutoxy)phenyl]-1,2-diphenyl-2-chloro-ethylene hydrochloride salt (138.4 g, 0.294 mol) and dichloromethane. Add with stirring a solution of sodium hydroxide (12.8 g) in water (100 mL). After 30 minutes, separate the layers and extract the aqueous layer with dichloromethane. Dry the combined organic layers over MgSO₄, filter, and evaporate in vacuo to give a residue. Combine the residue and acetone (1 L). Filter and combine the filtrate with a solution of citric acid (56.5 g, 0.294 mol) in acetone (2 L). Allow to stand at ambient temperature to give a solid. Collect the solid by filtration, rinse with acetone, and dry to give the title compound as a solid: mp; 133°–135° C.

EXAMPLE 4.2

(E)-1-[4-(4-Diethylaminobutoxy)phenyl]-1,2-diphenyl-2-chloro-ethylene citrate salt Combine (E and Z)-1-[4-(4-diethylaminobutoxy)phenyl]-1,2-diphenyl-2-chloro-ethylene hydrochloride salt (21.5 mol) and tetrahydrofuran (75 L). Heat to reflux. After 1 hour, cool to 30° C. to give a solid. Collect the solid by filtration, rinse with tetrahydrofuran, and dry. Combine the solid with tetrahydrofuran (83.2 L) and heat to reflux. After 18 hour, cool to 50° C. and filter, rinse with tetrahydrofuran, and dry to give (E)-1-[4-(4-diethylaminobutoxy)phenyl]-1,2-diphenyl-2-chloro-ethylene hydrochloride salt.

Combine (E)-1-[4-(4-diethylaminobutoxy)phenyl]-1,2-diphenyl-2-chloro-ethylene hydrochloride salt (138.4 g, 0.294 mol) and ethyl acetate (75 L). Add with stirring a solution of sodium hydroxide (3.0 kg, 75 mol) in water (20 L). After dissolution, separate the layers, dry the organic layer over MgSO₄, filter, and evaporate in vacuo to give a residue. Combine the residue and acetone (80 L). Filter and combine the filtrate with a solution of citric acid (3.6 kg, 18.8 mol) in acetone (20 L) and stir to give a solid. After 18 hours, collect the solid by filtration, rinse with acetone, and dry to give the title compound as a solid. Elemental Analysis calculated for $C_{28}H_{32}ClNO \cdot C_6H_8O_7$: C, 65.22; H, 6.44; N, 2.24. Found: C, 65.19; H, 6.29; N, 2.14.

EXAMPLE 5

(Z)-1-[4(4-Diethylaminobutoxy)phenyl]-1,2-diphenyl-2-chloro-ethylene citrate salt

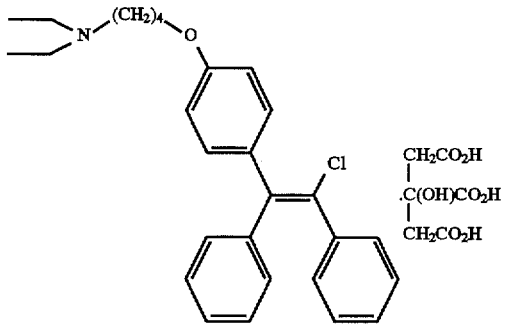

Combine citric acid (167.6 mg, 0.87 mmol) and ethanol (3 mL) and heat until the solid dissolves. Combine (Z)-1-[4-(4-diethylaminobutoxy)phenyl]-1,2-diphenyl-2-chloro-ethylene (378.7 mg, 0.87 mmol) and warm ethanol (3 mL) and add with stirring to the citric acid solution prepared above. Cool to 4° C. and allow to stand for 18 hours. Filter to give the title compound as a solid: mp; 150°–151° C.

EXAMPLE 6

(E and Z)-1-[4-(4-Ethylaminobutoxy)phenyl-1,2-diphenyl]-2-chloro-ethylene citrate salt

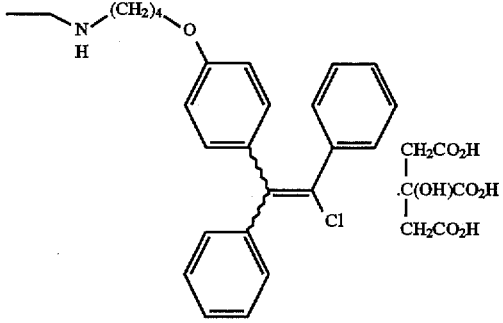

Combine (E and Z)-1-[4-(4-chlorobutoxy)phenyl]-1,2-diphenyl-2-chloro-ethylene (1.0 g, 2.5 mmol), ethylamine (15 mL, 193 mmol), potassium iodide (0.200 g), ethanol (2 mL), and water (5 mL). Heat to a gentle reflux. After 24 hours, cool to ambient temperature and concentrate in vacuo to obtain a residue. Chromatograph on silica gel eluting with 7% methanol/dichloromethane to obtain a residue. Combine the residue and butanone (6 mL). Add citric acid (0.52 g, 2.7 mmol) dissolved in butanone (4 mL). Allow to slowly evaporate until a solid forms, filter, and dry in vacuo to give the title compound.

EXAMPLE 7

(E and Z)-1-[4-(4-(Piperidin-1-yl)phenyl]-1,2-diphenyl-2-chloro-ethylene citrate salt

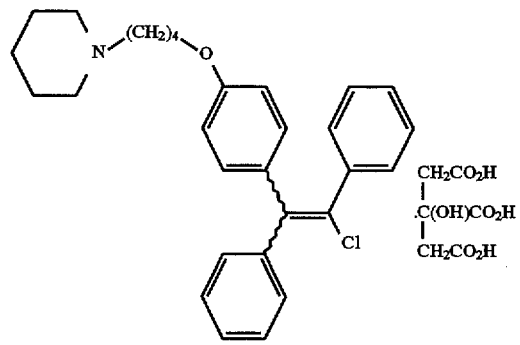

Combine (E and Z)-1-[4-(4-chlorobutoxy)phenyl]-1,2-diphenyl-2-chloro-ethylene (1.0 g, 2.5 mmol), piperidine (7.5 g), potassium iodide (0.200 g) and water (5 mL). Heat to 80° C. After 18 hours, cool to ambient temperature and partition the reaction mixture between water and ethyl acetate. Separate the organic layer and extract 3 times with water. Dry the organic layer over MgSO₄ and evaporate in vacuo. Chromatograph on silica gel eluting with 6% methanol/dichloromethane to obtain a residue (1.01 g). Combine the residue and butanone (6 mL). Add citric acid (0.423 g, 2.2 mmol) dissolved in butanone (2 mL). Evaporate in vacuo to give the title compound.

EXAMPLE 8

(E and Z)-1-[4-[4-(4-Methylpiperazin-1-yl)-butoxy)phenyl]-1,2-diphenyl-2-chloro-ethylene citrate salt

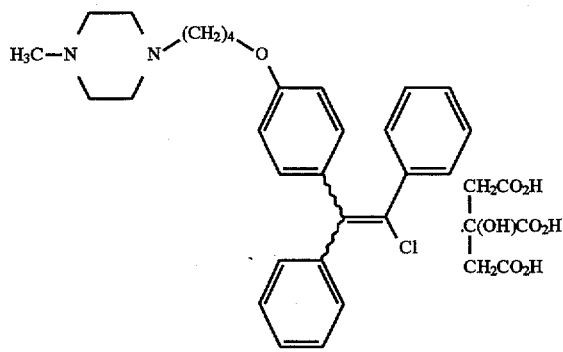

Combine (E and Z)-1-[4-(4-chlorobutoxy)phenyl]-1,2-diphenyl-2-chloro-ethylene (1.0 g, 2.5 mmol), 4-methylpiperazine (5 mL), potassium iodide (0.200 g), and water (3 mL). Heat to 80° C. After 18 hours, cool to ambient temperature and partition the reaction mixture between water and ethyl acetate. Separate the organic layer and extract 3 times with water. Dry the organic layer over $MgSO_4$ and evaporate in vacuo. Chromatograph on silica gel eluting with 5% methanol/dichloromethane to obtain a residue (0.758 g). Combine the residue and butanone (4 mL). Add citric acid (0.307 g, 1.6 mmol) dissolved in butanone (2 mL). Allow to slowly evaporate until a solid forms, filter, and dry in vacuo to give the title compound.

EXAMPLE 9

(E and Z)-1-[4-(4-(Pyrrolidin-1-yl)-butoxy)phenyl]-1,2-diphenyl-2-chloro-ethylene citrate salt

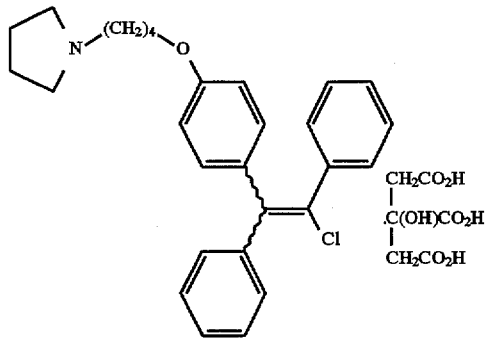

Combine (E and Z)-1-[4-(4-chlorobutoxy)phenyl]-1,2-diphenyl-2-chloro-ethylene (0.9 g, 2.25 mmol), pyrrolidine (5 mL), potassium iodide (0.200 g), and water (5 mL). Heat to 80° C. After 18 hours, cool to ambient temperature and partition the reaction mixture between water and ethyl acetate. Separate the organic layer and extract 3 times with water. Dry the organic layer over $MgSO_4$ and evaporate in vacuo. Chromatograph on silica gel eluting with 6% methanol/dichloromethane to obtain a residue (0.499 g). Combine the residue and butanone (2 mL). Add citric acid (0.211 g, 1.1 mmol) dissolved in butanone (2 mL). Allow to slowly evaporate until a solid forms, filter, and dry in vacuo to give the title compound.

EXAMPLE 10

(E and Z)-1-[4-(5-Chloropentoxy)phenyl]-1,2-diphenyl-2-chloro-ethylene

Combine (E and Z)-1-[(4-hydroxy)phenyl]-1,2-diphenyl-2-chloro-ethylene (2.3 g, 7.5 mmol) and 5-bromo-1-chloropentane (2.78 g, 15.0 mmol) in ethanol (40 mL). Add a solution of sodium ethoxide in ethanol (11.12 mL, 0.67M, 7.5 mmol). Heat to reflux under an inert atmosphere. After 24 hours concentrate in vacuo. Chromatograph on silica gel eluting with 1/7 ethyl acetate/hexane. Concentration of the product containing fractions to give the title compound which is taken on to the next step without further purification.

EXAMPLE 11

(E and Z)-1-[4-(5-Diethylaminopentoxy)phenyl]-1,2-diphenyl-2-chloro-ethylene

Combine (E and Z)-1-[4-(5-chloropentoxy)phenyl]-1,2-diphenyl-2-chloro-ethylene (3.08 g, 7.5 mmol), diethylamine (5.5 g, 75.0 mmol) and potassium iodide (30 mg, 0.178 mmol) in water (8.0 mL). Heat to 40° C. for 4 hours and then cool to ambient temperature and allow to stand for 72 hours. Add diethylamine (10 mL) and heat to 80° C. After 3 hours chromatograph on silica gel eluting first with 20% ethyl acetate/hexane and then with 20% ethyl acetate/hexane containing 5% triethylamine. Combine product containing fractions and concentrate in vacuo. Chromatograph, again, on silica gel eluting with 7% methanol/dichloromethane. Concentration of product containing fractions to give a mixture of the isomers as a residue. Separate the isomers by HPLC, 90 mg per injection, using a Waters and Associates μPorasil column (19 mm by 300 mm), eluting with 80/20/0.2 chloroform/hexane/triethylamine at 20 mL/minute to give (E)-1-[4-(5-diethylaminopentoxy)phenyl]-1,2-diphenyl-2-chloro-ethylene and (Z)-1-[4-(5-diethylaminopentoxy)phenyl]-1,2-diphenyl-2-chloro-ethylene.

EXAMPLE 12

(E)-1-[4-(5-Diethylaminopentoxy)phenyl]-1,2-diphenyl-2-chloro-ethylene citrate salt

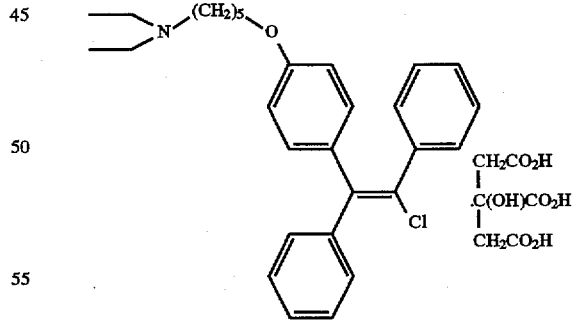

Combine citric acid (192.13 mg, 1.21 mmol) and isopropanol (3 mL) and heat until the solid dissolves. Combine (E)-1-[4-(5-diethylaminopentoxy)phenyl]-1,2-diphenyl-2-chloro-ethylene (543.2 mg, 1.21 mmol) and warm isopropanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 124°–127° C.

EXAMPLE 13

(Z)-1-[4-(5-Diethylaminopentoxy)phenyl]-1,2-diphenyl]-2-chloro-ethylene citrate salt

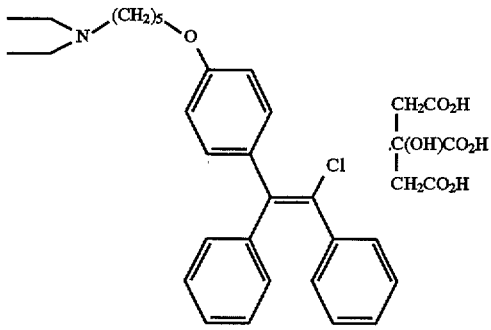

Combine citric acid (192.13 mg, 1.21 mmol) and isopropanol (3 mL) and heat until the solid dissolves. Combine (Z)-1-[4-(5-diethylaminopentoxy)phenyl]-1,2-diphenyl-2-chloro-ethylene (543.2 mg, 1.21 mmol) and warm isopropanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 124°–127° C.

EXAMPLE 14

1,1-Bis-(4-methoxy)phenyl-2-phenyl-ethanol

Combine benzylmagnesium chloride (180 mL, 2M in tetrahydrofuran, 360 mmol) and 4,4'-dimethoxybenzophenone (50 g, 207 mmol), Heat to a gentle reflux. After 72 hours, carefully pour the reaction mixture onto a mixture of ice (300 g) and a saturated aqueous solution of ammonium chloride (50 mL). Extract with diethyl ether, dry the organic layer over $MgSO_4$, and evaporate in vacuo to give the title compound.

EXAMPLE 15

1,1-Bis-(4-methoxy)phenyl-2-phenyl-ethylene

Combine 1,1-bis-(4-methoxy)phenyl-2-phenyl-ethanol obtained in Example 14 and 12M hydrochloric acid (50 mL) is ethanol (400 mL). Heat to reflux. After 24 hours, cool the reaction mixture to ambient temperature. Evaporate in vacuo to obtain a reside. Partition the residue between water and ethyl acetate. Separate the organic layer, dry over the $MgSO_4$, and evaporate in vacuo to give the title compound.

EXAMPLE 16

1,1-Bis-(4-methoxy)phenyl-2-phenyl-2-chloro-ethylene

Combine 1,1-bis-(4-methoxy)phenyl-2-phenyl-ethylene (24 g, 75.8 mmol) and N-chlorosuccinimide (10.7 g, 80 mmol) in chloroform (100 mL). Heat to 60° C. After 18 hours, cool to ambient temperature and evaporate in vacuo. Chromatograph on silica gel eluting with 1/10 ethyl acetate/hexane to give the title compound.

EXAMPLE 17

1,1-Bis-(4-hydroxy)phenyl-2-phenyl-2-chloro-ethylene

Heat pyridinium hydrochloride (140 g, 1210 mmol) to 220° C. Add portionwise, 1,1-bis-(4-methoxy)phenyl-2-phenyl-2-chloro-ethylene (37.5 g, 107 mmol) and maintain the temperature at 220° C. After 45 minutes, pour the reaction mixture onto ice (400 g). Extract with ethyl acetate. The organic layer is extracted with water and 0.5M hydrochloric acid solution. Separate the organic layer, dry over the $MgSO_4$, and evaporate in vacuo to give the title compound.

EXAMPLE 18

(E and Z)-1-[4-(4-Chlorobutoxy)phenyl]-1-(4-hydroxy)phenyl-2-phenyl-2-chloro-ethylene and 1,1-Bis-[4-(4-chlorobutoxy)phenyl]-2-phenyl-2-chloro-ethylene Add sodium metal (0.440 g, 19 mmol) and ethanol (80 mL) and stir until the sodium metal has reacted. Add 1,1-bis-(4-hydroxy)phenyl-2-phenyl-2-chloro-ethylene (5.56 g, 17.2 mmol) and heat the reaction mixture to 40° C. for 15 minutes. Add 1-bromo-4-chlorobutane (0.34 g, 20 mmol) and heat to a gentle reflux. After 72 hours, evaporate in vacuo. Chromatograph on silica gel eluting with dichloromethane to give (E and Z)-1-[4-(4-chlorobutoxy)phenyl]-1-(4-hydroxy)phenyl-2-phenyl-2-chloro-ethylene (2.5 g) and 1,1-bis-[4-(4-chlorobutoxy)phenyl]-2-phenyl-2-chloro-ethylene (0.96 g).

EXAMPLE 19

(E and Z)-1-[4-(4-Diethylaminobutoxy)phenyl]-1-(4-hydroxy)phenyl-2-phenyl-2-chloro-ethylene Combine (E and Z)-1-[4-(4-chlorobutoxy)phenyl]-1-(4-hydroxy)phenyl-2-phenyl-2-chloro-ethylene (2.5 g, 6 mmol), diethylamine (50 mL), potassium iodide (0.50 g), and water (50 mL). Heat to a gentle reflux. After 16 hours, cool the reaction mixture to ambient temperature. Partition the reaction mixture between water and ethyl acetate. Separate the organic layer, dry over $MgSO_4$, and evaporate in vacuo. Chromatograph on silica gel eluting with 15% methanol/dichloromethane to give a residue. Combine the residue and chloroform (50 mL). Divide the chloroform solution in half. Evaporate one half in vacuo to obtain a residue. Combine the residue obtained from the chloroform solution and butanone (7 mL). Add citric acid (0.345 g) dissolved in butanone (4 mL) and methanol (1 mL). Allow to stand until a solid forms, collect by filtration and dry in vacuo to give the title compound. Evaporate one half in vacuo to obtain a residue for separation of the isomers on HPLC. Separate the isomers by HPLC, 20 mg per injection, using a 5 µm Spherisorb CN (column #61037) (21.2 mm by 250 mm), eluting with 55/40/5 chloroform/hexane/methanol containing 0.05% triethylamine at 20 mL/minute to give (E)-1-[4-(4-diethylaminobutoxy)phenyl]-1-(4-hydroxy)phenyl-2-phenyl-2-chloro-ethylene and (Z)-1-[4-(4-diethylaminobutoxy)phenyl]-1-(4-hydroxy)phenyl-2-phenyl-2-chloro-ethylene.

EXAMPLE 19.1

(E and Z)-1-[4-(4-Diethylaminobutoxy)phenyl]-1-(4-hydroxy)phenyl-2-phenyl-2-chloro-ethylene Combine 4,4'dihydroxybenzophenone (21.4 g, 0.10 mmol) and sodium hydroxide (4.0 g, 0.10 mmol) in water (50 mL). Heat to 80° C. Add toluene (100 mL). Add benzyl chloride (17.3 mL, 0.15 mmol) in toluene/methanol (100 mL/40 mL). Maintain heating at 70° C. to 80° C. After 3 days, cool to ambient temperature and partition the reaction mixture between ethyl acetate and water. Separate the layers and extract the aqueous layer with ethyl acetate. Combine the organic layers and extract with aqueous 1M sodium hydroxide solution and then water. Evaporate the organic layers in vacuo to give a reside. Combine the aqueous layers and allow to stand to give a solid. Collect the solid by filtration, rinse with water, and dry to give a solid. Combine the solid and the residue obtained from evaporation of the organic layers and recrystallize from toluene to give 4-benzyloxy-4'-hydroxybenzophenone: $R_f$=0.21 (silica gel, 30% ethyl acetate/hexane).

Combine 4-benzyloxy-4'-hydroxybenzophenone (9.12 g, 30.0 mmol) and sodium hydroxide (1.8 g, 45 mmol) in water (35 mL). Add tetrabutylammonium hydrogensulfate (1.02 g, 3.0 mmol). Add 1-bromo-4-chlorobutane (5.2 mL, 45 mmol). Heat to reflux. After 3 hours, cool the reaction mixture to give a solid. Collect the solid by filtration, rinse with water, and dry to give 4-benzyloxy-4'-(4-chlorobutyloxy)benzophenone: $R_f$=0.32 (silica gel, 30% ethyl acetate/hexane).

Combine 4-benzyloxy-4'-(4-chlorobutyloxy) benzophenone (3.95 g, 10.0 mmol) and tetrahydrofuran (50 mL). Add a solution benzylmagnesium chloride (6.0 mL, 2M in tetrahydrofuran, 12 mmol). After 1 hour, cool to 0° C. and add a saturated aqueous solution of ammonium chloride and stir for 1 hour to give a solid. Filter the solid and rinse three times with tetrahydrofuran. Combine the filtrate and rinses and separate the layers. Extract the organic layer with a saturated sodium chloride solution. Dry the organic layer over $MgSO_4$, filter, and dry in vacuo to give a 1-(4-benzyloxyphenyl)-1-(4-(4-chlorobutyloxy) phenyl)-2-phenyl ethanol: $R_f$=0.36 (silica gel, 30% ethyl acetate/hexane).

Combine 1-(4-benzyloxyphenyl)-1-(4-(4-chlorobutyloxy) phenyl)-2-phenyl ethanol (1.0 g, 21.0 mmol) and methanol (2 mL). Add aqueous 2M hydrochloric acid solution (4 mL). Heat to reflux. After 2 hours, concentrate at 65° C. to remove most of the methanol. Cool to ambient temperature and extract with dichloromethane. Dry the organic layer over $MgSO_4$, filter, and dry in vacuo to give 1-(4-benzyloxyphenyl)-1-(4-(4-chlorobutyloxy) phenyl)-2-phenyl ethylene: $R_f$=0.50 (silica gel, 30% ethyl acetate/hexane).

Combine 1-(4-benzyloxyphenyl)-1-(4-(4-chlorobutyloxy)phenyl)-2-phenyl ethylene (3.5 g, 7.5 mmol) and chloroform 935 mL). Add N-chlorosuccinimide (1.99 g, 14.9 mmol). Heat at reflux. After 18 hours, cool the reaction mixture and extract with water, aqueous saturated sodium bicarbonate solution and water. Dry the organic layer over $MgSO_4$, filter, and dry in vacuo to give a residue. Chromatograph the residue on silica gel eluting with 10% ethyl acetate/hexane to give 1-(4-benzyloxyphenyl)-1-(4-(4-chlorobutyloxy)phenyl)-2-chloro-2-phenyl ethylene.

Combine 1-(4-benzyloxyphenyl)-1-(4-(4-chlorobutyloxy)phenyl)-2-chloro-2-phenyl ethylene (0.1 g, 0.20 mmol), 5% palladium-on-carbon (30 mg), and ethyl acetate (1.5 mL). Treat with hydrogen at atmospheric pressure. After 1.5 hours, filter using a 0.45 micron membrane. Concentrate the filtrate in vacuo to give 1-(4-hydroxyphenyl)-1-(4-(4-chlorobutyloxy)phenyl)-2-chloro-2-phenyl ethylene.

Combine with diethylamine by the method of Example 19 to give the title compound.

EXAMPLE 20

(E)-1-[4-(4-Diethylaminobutoxy)phenyl]-1-(4-hydroxy) phenyl-2-phenyl-2-chloro-ethylene citrate salt

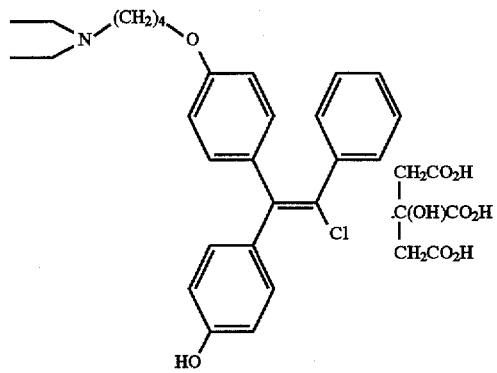

Combine citric acid (48 mg, 0.25 mmol) and butanone (10 mL). Combine (E)-1-[4-(4-diethylaminobutoxy)phenyl]-1-(4-hydroxy)phenyl-2-phenyl-2-chloro-ethylene (115 mg, 0.26 mmol). Allow to stand until a solid forms, filter to give the title compound as a solid: mp; 94°–96° C.

EXAMPLE 21

(Z)-1-[4-(4-Diethylaminobutoxy)phenyl]-1-(4-hydroxy) phenyl-2-phenyl-2-chloro-ethylene citrate salt

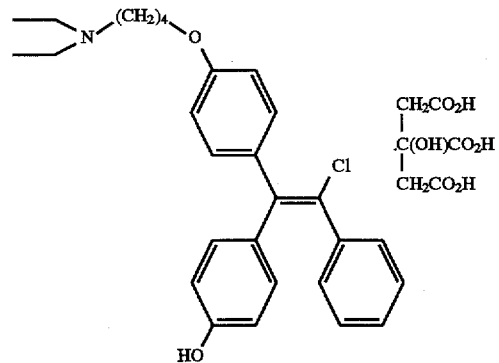

Combine citric acid (48 mg, 0.25 mmol) and butanone (10 mL). Combine (E)-1-[4-(4-diethylaminobutoxy)phenyl]-1-(4-hydroxy)phenyl-2-phenyl-2-chloro-ethylene (118 mg, 0.26 mmol). Allow to stand until a solid forms, filter to give the title compound as a solid: mp; 90°–92° C.

EXAMPLE 22

1,1-Bis-[4-(4-diethylaminobutoxy)phenyl]-2-phenyl-2-chloro-ethylene

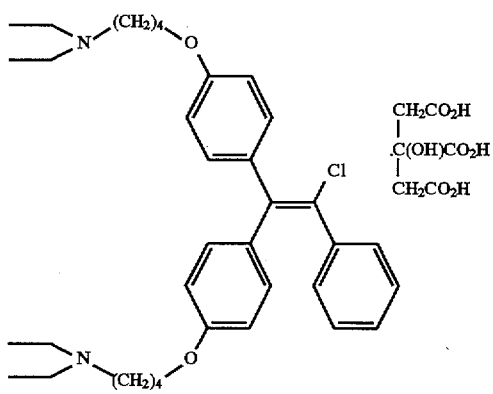

Combine 1,1-bis-[4-(4-chlorobutoxy)phenyl]-2-phenyl-2-chloro-ethylene (0.950 g, 1.89 mmol), diethylamine (15 mL), potassium iodide (0.10 g), ethanol (5 mL), and water (15 mL). Heat to a gentle reflux. After 8 hours, cool the reaction mixture to ambient temperature. Partition the reaction mixture between water and ethyl acetate. Separate the organic layer, dry over the $MgSO_4$, and evaporate in vacuo. Chromatograph on silica gel eluting with 20% methanol/dichloromethane to give a residue. Combine the residue and butanone (5 mL). Add citric acid (0.110 g) dissolved in butanone (5 mL). Heat and add methanol until dissolution. Allow to slowly evaporate until a solid forms, collect by filtration and dry in vacuo to give the title compound.

EXAMPLE 23

4-(4-Bromobutoxy)benzophenone

Combine 4-hydroxybenzophenone (14.11 g, 71.2 mmol) and aqueous 1M sodium hydroxide solution (70 mL). Add 1,4-dibromobutane (43.4 g, 200 mmol). Heat the reaction mixture to reflux. After 20.5 hours, cool to ambient temperature. Add pentane (100 mL) and again heat to reflux. After 0.5 hours, cool to ambient temperature to give a solid. Collect the solid by filtration recrystallize the solid from ethanol to give the title compound: mp; 42°–43° C.

EXAMPLE 24

1-(4-Bromobutoxy)phenyl-1-phenyl-2-(3-methoxyphenyl)-ethanol

Combine magnesium turnings (5.8 g, 240 mmol) and diethyl ether (35 mL). Heat to reflux. Add about 5 mL of a solution of 3-methoxybenzyl chloride (6.5 g, 41 mmol) in diethyl ether (50 mL) along with one small iodine crystal. After the reaction starts, slowly add over about 2.5 hours, the remainder of the solution of 3-methoxybenzyl chloride. After the addition is complete continue to heat at a gentle reflux. After 14 hours, cool to ambient temperature and add to a solution of 4-(4-bromobutoxy)benzophenone (12.5 g, 37.6 mmol) in tetrahydrofuran (100 mL). After 7 hours, carefully pour the reaction mixture into a saturated aqueous solution of ammonium chloride (50 mL). Extract with ethyl acetate, dry the organic layer over $MgSO_4$, and evaporate in vacuo to give a residue. Chromatograph the residue on silica gel eluting with 10% ethyl acetate/hexane to give the title compound.

EXAMPLE 25

(E and Z)-1-(4-Bromobutoxy)phenyl-1-phenyl-2-(3-methoxyphenyl)-ethylene

Combine 1-(4-bromobutoxy)phenyl-1-phenyl-2-(3-methoxyphenyl)-ethanol (7.2 g, 15.7 mmol) and dichloromethane (100 mL). Add trifluoroacetic anhydride (5 mL, 35 mmol). Heat to reflux. After 21 hours, cool the reaction mixture to ambient temperature. Evaporate in vacuo to obtain a reside. Partition the residue between water and ethyl acetate. Separate the organic layer, extract with aqueous sodium bicarbonate solution, dry over the $MgSO_4$, and evaporate in vacuo to give a residue. Chromatograph the residue on silica gel eluting with 10% ethyl acetate/hexane to give the title compound.

EXAMPLE 26

(E and Z)-1-(4-Bromobutoxy)phenyl-1-phenyl-2-(3-methoxyphenyl)-2-chloro-ethylene Combine (E and Z)-1-(4-bromobutoxy)phenyl-1-phenyl-2-(3-methoxyphenyl)-ethylene (0.15 g, 0.34 mmol) and N-chlorosuccinimide (0.11 g, 0.8 mmol) in chlorobenzene (4 mL). Heat to reflux. After 67 hours, cool to ambient temperature and pour the reaction into diethyl ether. Extract the organic layer with aqueous 1M sodium hydroxide solution. Dry the organic layer over the $MgSO_4$, filter, and evaporate in vacuo to give a residue. Chromatograph the residue on silica gel eluting with 20% ethyl acetate/hexane to give the title compound.

EXAMPLE 27

(E and Z)-1-(4-Iodobutoxy)phenyl-1-phenyl-2-(3-trimethylsiloxyphenyl)-2-chloro-ethylene Combine (E and Z)-1-(4-bromobutoxy)phenyl-1-phenyl-2-(3-methoxyphenyl)-2-chloro-ethylene (0.26 g, 0.56 mmol). pyridine (0.04 g, 0.62 mmol), and chloroform (4.0 mL). Add trimethylsilyl iodide (0.49 g, 2.5 mmol). After 19 hours, heat the reaction mixture to reflux. After 2 hours, add an additional portion of trimethylsilyl iodide (1.4 g, 7.0 mmol). After 67 hours, cool the reaction mixture to ambient temperature and evaporate in vacuo to give the title compound.

EXAMPLE 28

(E and Z)-1-(4-Diethylaminobutoxy)phenyl-1-phenyl-2-(3-hydroxyphenyl)-2-chloro-ethylene

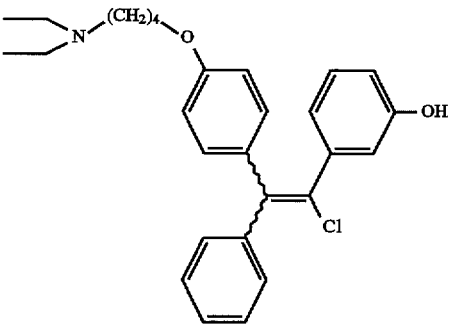

Combine (E and Z)-1-(4-iodobutoxy)phenyl-1-phenyl-2-(3-trimethylsiloxyphenyl)-2-chloro-ethylene prepared in Example 27 and diethyl amine (10 mL, 96 mmol). Heat to reflux. After 18 hours, evaporate in vacuo to give a residue. Combine the residue and ethyl acetate. Extract with water. Extract two times with aqueous 1M hydrochloric acid solution. Combine the acid layers and extract with diethyl ether. Neutralize the acid extract with aqueous 1M sodium hydroxide solution and extract twice with ethyl acetate. Combine the ethyl acetate layers, dry over $MgSO_4$, filter, and evaporate in vacuo to give a residue. Chromatograph the residue on silica gel to give the title compound.

Alternately, the compounds of Formula I and Formula II in which Y is O can be prepared as described in Scheme B. All substituents, unless otherwise indicated, are previously defined. The reagents and starting materials are readily available to one of ordinary skill in the art.
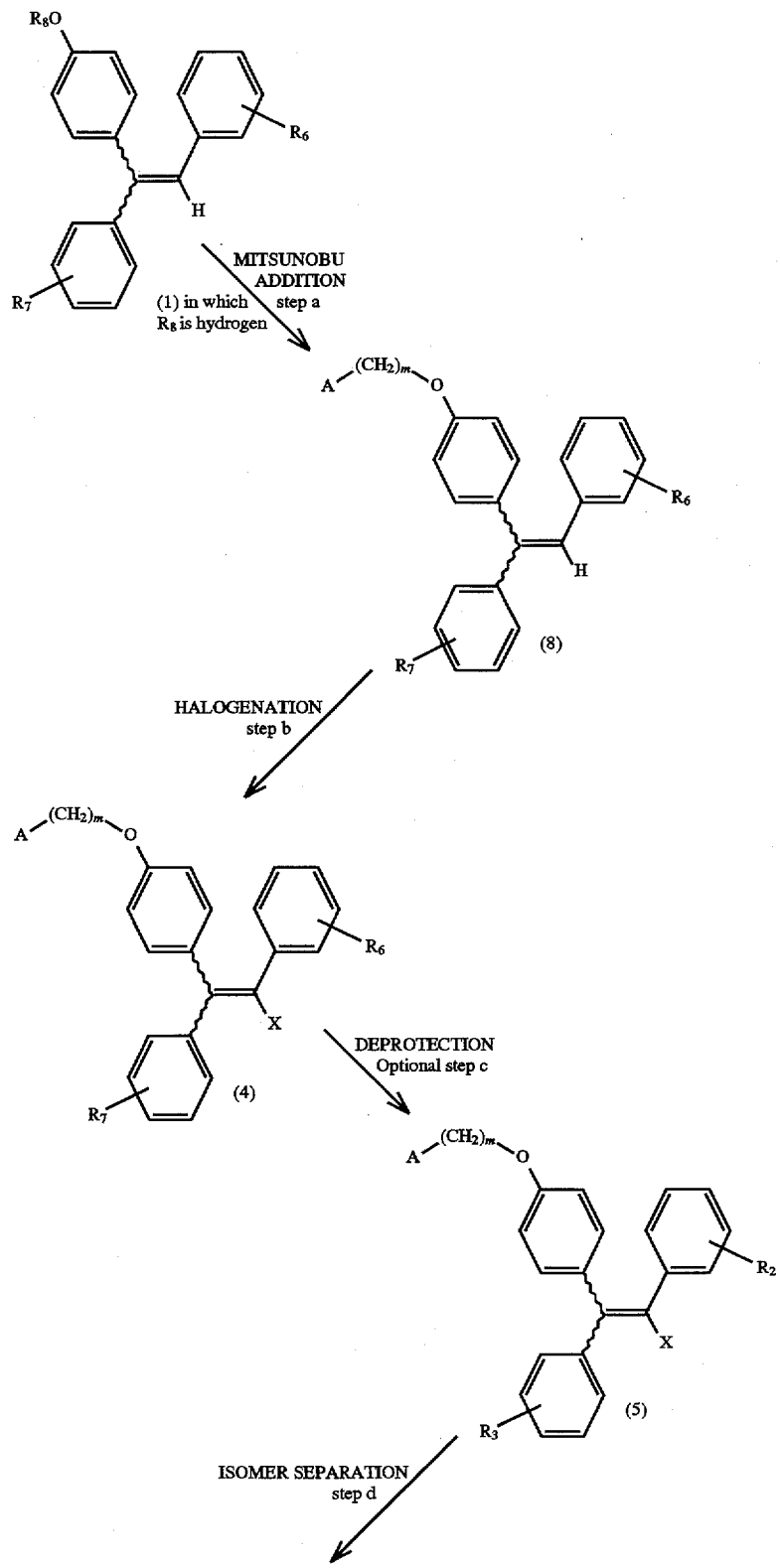

-continued
SCHEME B

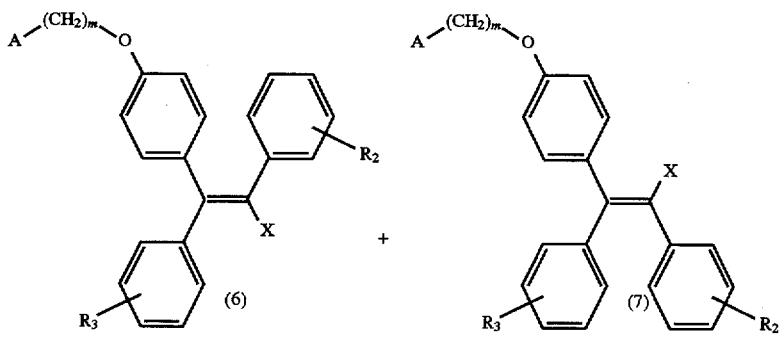

In Scheme B, step a, an appropriate ω-aminoalcohol is added by a Mitsunobu addition to an appropriate triaryl-ethylene of structure 1 in which $R_8$ is hydrogen to give a ω-aminoalkoxy-triaryl-ethylene of structure 8.

An appropriate ω-aminoalcohol, HO—$(CH_2)_m$—A, is one in which A and m are as desired in the final product of Formula I and Formula II. An appropriate triaryl-ethylene of the structure 1 is one in which $R_8$ is hydrogen; $R_6$ is as defined for $R_2$, or $R_6$ is a suitably protected hydroxy which after deprotection provide compounds of Formula I and Formula II in which $R_2$ is a hydroxy group; and $R_7$ is as defined for $R_3$, or $R_7$ is a suitably protected hydroxy which after deprotection provide compounds of Formula I and Formula II in which $R_3$ is a hydroxy group, or provides an intermediate for the preparation of a compound of Formula I and Formula II in which $R_3$ is —$O(CH_2)_pA_1$ wherein p=m and A=$A_1$; or $R_7$ is a suitably protected hydroxy which allows for removal in a sequential manner providing an intermediate for the preparation of compounds of Formula I and Formula II in which $R_3$ is —$O(CH_2)_pA_1$ wherein p≠m and either A=$A_1$ or A≠$A_1$, or in which $R_3$ is —$O(CH_2)_pA_1$ wherein p=m and A≠$A_1$. The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

For example, an appropriate ω-aminoalcohol is contacted with a molar equivalent of a triaryl-ethylene of structure 1 in which $R_8$ is hydrogen and a molar equivalent of triphenylphosphine in a suitable solvent, such as tetrahydrofuran (THF). Diethyl azodicarboxylate neat or as a solution in a suitable solvent, such as tetrahydrofuran is added. After stirring for from 1–72 hours the product can be isolated and purified by techniques well known in the art. For the preparation of compounds of Formula I and Formula II in which $R_3$ is —$O(CH_2)_pA_1$ wherein p=m and A=$A_1$ a compound in which $R_7$ is hydroxy is used along with an additional equivalent of an appropriate ω-aminoalcohol, triphenylphosphine, and diethyl azodicarboxylate are used. The reaction mixture can be concentrated in vacuo to give a residue. The residue can be chromatographed on silica gel using a suitable organic eluent. The material obtained from chromatography can be recrystallized to give a ω-aminoalkoxy-triaryl-ethylene of structure 8.

In Scheme B, step b, a ω-aminoalkoxy-triaryl-ethylene of structure 8 is chlorinated or brominated to give a ω-aminoalkoxy-triaryl-ethylene of structure 4.

For example, a ω-aminoalkoxy-triaryl-ethylene of structure 8 is contacted with a molar excess of chlorine, bromine, N-chlorosuccinimide, or N-bromosuccinimide in a suitable solvent, such as chloroform or dichloromethane. The reaction is carried out at temperatures from ambient temperature to the reflux temperature of the solvent. After stirring for from 12–72 hours the product can be isolated and purified by techniques well known in the art. For example, the reaction mixture can be concentrated in vacuo and the product purified by techniques well known in the art, such as salt formation, chromatography eluting with a suitable solvent, or recrystallization from a suitable organic solvent.

In Scheme B, steps a and b, can be carried out in any order.

In Scheme B, Optional step c, for a ω-aminoalkoxy-triaryl-ethylene of structure 4 in which $R_6$ or $R_7$ are a protected hydroxy group the protecting group is removed in a deprotection step to provide a ω-aminoalkoxy-triaryl-ethylene of structure 5 in which either, $R_2$ or $R_3$, or $R_2$ and $R_3$, are hydroxy as desired in the final product of Formula I and Formula II. The production of a compound of Formula I and II in which $R_3$ is —$O(CH_2)_pA_1$ wherein p≠m and either A=$A_1$ or A≠$A_1$ or in which $R_3$ is —$O(CH_2)_pA_1$ wherein p=m and either A=$A_1$ or A≠$A_1$ may require the removal of protecting groups in a sequential manner to provide a compound of the structure 4 in which $R_7$ is a hydroxy group. As is apparent to one skilled in the art a compound of the structure 4 in which $R_7$ is a hydroxy group can be subjected to steps b and c of Scheme A or step a of Scheme B to give a bis-ω-aminoalkoxy-triaryl-ethylene compound of Formula I and II in which $R_3$ is —$O(CH_2)_pA_1$ wherein p≠m and either A=$A_1$ or A≠$A_1$ or in which $R_3$ is —$O(CH_2)_pA_1$ wherein p=m and A≠$A_1$ or a bis-ω-aminoalkoxy-triaryl-ethylene compound of Formula I and II wherein p=m and A=$A_1$.

The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

In Scheme B step d, the isomers of a ω-aminoalkoxy-triaryl-ethylene of structure 4 or 5 are separated to give the (E)-ω-aminoalkoxy-triaryl-ethylene and the (Z)-ω-aminoalkoxy-triaryl-ethylene as taught in Scheme A step e.

Pharmaceutically acceptable salts of a (E)-ω-aminoalkoxy-triaryl-ethylene or a (Z)-ω-aminoalkoxy-triaryl-ethylene can be formed in an additional step as is well known and practiced in the art.

The following examples present typical syntheses as described in Scheme B. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "mp" refers to melting point, "HPLC" refers to high performance liquid chromatography.

EXAMPLE 29

(E and Z)-1-[4-(6-Diethylaminohexoxy)phenyl]-12-diphenyl-ethylene

Combine (E and Z)-1-[(4-hydroxy))phenyl]-1,2-diphenyl-ethylene (3.05 g, 11.2 mmol), 6-diethylaminohexanol (2.0 g, 11.5 mmol), and triphenylphosphine (3.73 g, 14.2 mmol) in THF (25 mL). Add dropwise diethyl azodicarboxylate (2.24 mL, 14.2 mmol). Stir for 24 hours. Concentrate in vacuo. Chromatograph on silica gel eluting with 7% methanol/dichloromethane. Concentration of the product containing fractions to give the title compound.

EXAMPLE 30

(E and Z)-1-[4-(6-Diethylaminohexoxy)phenyl]-1,2-diphenyl-2-chloro-ethylene

Combine (E and Z)-1-[4-(6-diethylaminohexoxy)phenyl]-1,2-diphenyl-ethylene (2.17 g, 5.07 mmol), N-chlorosuccinimide (0.745 g, 5.57 mmol), and chloroform (40 mL). Heat to reflux for 18 hours. Cool to ambient temperature. Add N-chlorosuccinimide (0.745 g, 5.57 mmol). Heat to reflux. After 2 hours evaporate in vacuo. Chromatograph on silica gel eluting with 10% methanol/dichloromethane. Combine product containing fractions and concentrate in vacuo to give the title compound. Separate the isomers by HPLC, 90 mg per injection, using a Waters and Associates µPorasil column (19 mm by 300 mm), eluting with 80/20/0.2 chloroform/hexane/triethylamine at 20 mL/minute to give (E)-1-[4-(6-diethylaminohexoxy)phenyl]-1,2-diphenyl-2-chloro-ethylene and (Z)-1-[4-(6-diethylaminohexoxy)phenyl]-1,2-diphenyl-2-chloro-ethylene.

EXAMPLE 31

(E)-1-[4-(6-Diethylaminohexoxy)phenyl]-1,2-diphenyl-2-chloro-ethylene citrate salt

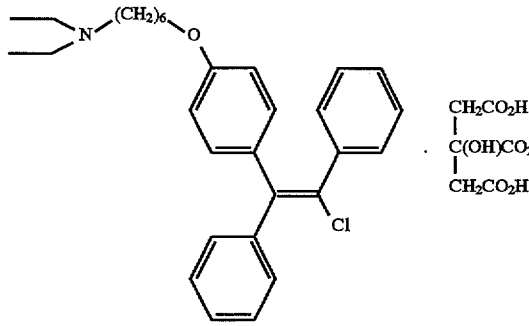

Combine citric acid (370 mg, 0.80 mmol) and ethanol (4 mL) and heat until the solid dissolves. Combine (E)-1-[4-(6-diethylaminohexoxy)phenyl]-1,2-diphenyl-2-chloro-ethylene (154 mg, 0.80 mmol) and warm ethanol (5 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 84°–87° C.

EXAMPLE 32

(Z)-1-[4-(6-Diethylaminohexoxy)phenyl]-1,2-diphenyl-2-chloro-ethylene citrate salt

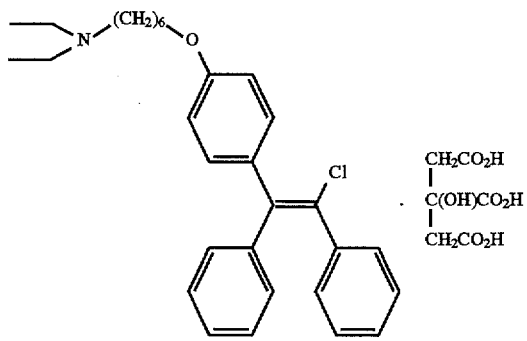

Combine citric acid (56 mg, 0.29 mmol) and ethanol (2 mL) and heat until the solid dissolves. Combine (Z)-1-[4-(6-diethylaminohexoxy)phenyl]-1,2-diphenyl-2-chloro-ethylene (134 mg, 0.29 mmol) and warm ethanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 84°–87° C.

EXAMPLE 33

(E and Z)-1-[4-(7-Diethylaminoheptoxy)phenyl]-1,2-diphenyl-2-chloro-ethylene

Prepare by the methods taught in Example 29, using 7-diethylaminoheptanol, and Example 24 to give the title compound. Separate the isomers by HPLC, using multiple injections, using a Waters and Associates µProasil column (19 mm by 300 mm), eluting with 19/4.8/76.2/0.1 ethyl acetate/chloroform/hexane/triethylamine at 20 mL/minute to give (E)-1-[4-(7-diethylaminoheptoxy)phenyl]-1,2-diphenyl-2-chloro-ethylene and (Z)-1-[4-(7-diethylaminoheptoxy)phenyl]-1,2-diphenyl-2-chloro-ethylene.

EXAMPLE 34

(E)-1-[4-(7-Diethylaminoheptoxy)phenyl]-1,2-diphenyl-2-chloro-ethylene citrate salt

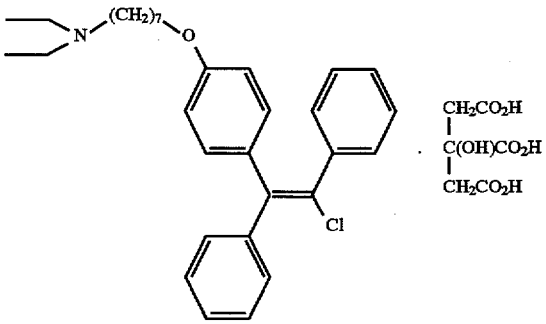

Combine (E)-1-[4-(7-diethylaminoheptoxy)phenyl]-1,2-diphenyl-2-chloro-ethylene (0.225 g) and hot isopropyl alcohol (4 mL). Add a solution of citric acid (0.090 g) in hot isopropyl alcohol (2 mL). Allow to cool and evaporate until a solid forms. Filter and dry to give the title compound: mp; 106°–108° C.

EXAMPLE 35

(Z)-1-[4-(7-Diethylaminoheptoxy)phenyl]-1,2-diphenyl-2-chloro-ethylene citrate salt

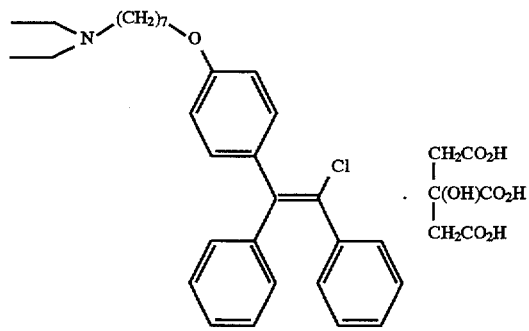

Combine (Z)-1-[4-(7-diethylaminoheptoxy)phenyl]-1,2-diphenyl-2-chloro-ethylene (0.087 g) and hot isopropyl alcohol (3 mL). Add a solution of citric acid (0.035 g) in hot isopropyl alcohol (1 mL). Allow to cool and evaporate until a solid forms. Filter and dry to give the title compound: mp; 94°–96° C.

EXAMPLE 36

(E and Z)-1-[4-(8-Diethylaminooctoxy)phenyl]-1,2-diphenyl-2-chloro-ethylene

Prepare by the methods taught in Example 9, using 8-diethylaminooctanol, and Example 30 to give the title compound. Separate the isomers by HPLC, using multiple injections, using a 5 µm Spherisorb CN (21.2 mm by 250 mm), eluting with 50/50/chloroform/hexane containing 0.1% triethylamine at 20 mL/minute to give (E)-1-[4-(7-diethylaminoheptoxy)phenyl]-1,2-diphenyl-2-chloro-ethylene and (Z)-1-[4-(7-diethylaminoheptoxy)phenyl]-1,2-diphenyl-2-chloro-ethylene.

EXAMPLE 37

(E)-1-[4-(8-Diethylaminooctoxy)phenyl]-1,2-diphenyl-2-chloro-ethylene citrate salt

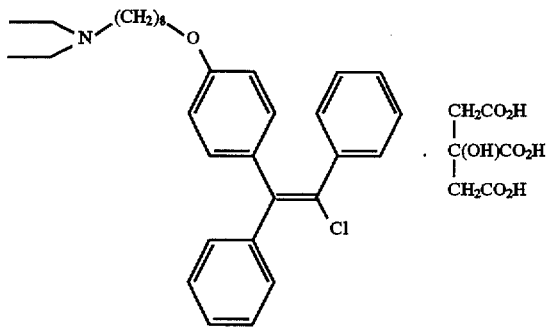

The citrate salt is formed in butanone (2 mL) using (E)-1-[4-(8-diethylaminooctoxy)phenyl]-1,2-diphenyl-2-chloro-ethylene (0.063 g) and citric acid (0.025 g) to give the title compound: mp; 90°–92° C.

EXAMPLE 38

(Z)-1-[4-(8-Diethylaminooctoxy)phenyl]-1,2-diphenyl-2-chloro-ethylene citrate salt

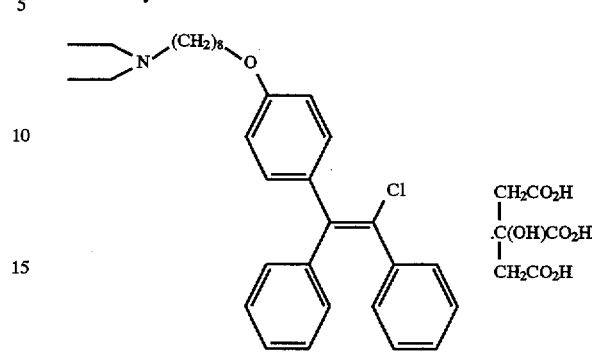

The citrate salt is formed in butanone (0.5 mL) using (Z)-1-[4-(8-diethylaminooctoxy)phenyl]-1,2-diphenyl-2-chloro-ethylene (0.049 g) and citric acid (0.0094 g): mp; 105°–107° C.

EXAMPLE 39

(E and Z)-1-[4-(9-Diethylaminononoxy)phenyl]-1,2-diphenyl-2-chloro-ethylene

Prepare by the methods taught in Example 29, using 9-diethylaminonanol, and Example 30 to give the title compound. Separate the isomers by HPLC, using multiple injections, using a 5 µm Spherisorb CN (21.2 mm by 250 mm), eluting with 40/60/chloroform/hexane containing 0.1% triethylamine at 20 mL/minute to give (E)-1-[4-(9-diethylaminononoxy)phenyl]-1,2-diphenyl-2-chloro-ethylene and (Z)-1-[4-(9-diethylaminononoxy)phenyl]-1,2-diphenyl-2-chloro-ethylene.

EXAMPLE 40

(E)-1-[4-(9-Diethylaminononoxy)phenyl]-1,2-diphenyl-2-chloro-ethylene citrate salt

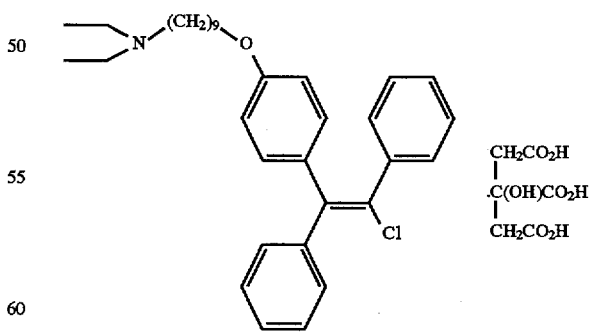

The citrate salt is formed in butanone (2 mL) using (E)-1-[4-(9-diethylaminononoxy)phenyl]-1,2-diphenyl-2-chloro-ethylene (0.105 g) and citric acid (0.040 g) in butanone (2 mL) to give the title compound: mp; 92°–3° C.

EXAMPLE 41

(Z)-1-[4-(9-Diethylaminononoxy)phenyl]-1,2-diphenyl-2-chloro-ethylene citrate salt

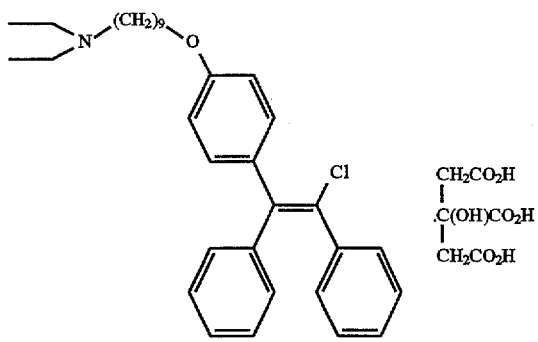

The citrate salt is formed in butanone (0.5 mL) using (Z)-1-[4-(9-diethylaminononoxy)phenyl]-1,2-diphenyl-2-chloro-ethylene (0.036 g) and citric acid (0.013 g) in butanone (2 mL) to give the title compound: mp; 83°–85° C.

EXAMPLE 42

(E and Z)-1-[4-(10-Diethylaminodecoxy)phenyl]-1,2-diphenyl-2-chloro-ethylene

Prepare by the methods taught in Example 29, using 10-diethylaminodecanol, and Example 30 to give the title compound. Separate the isomers by HPLC using multiple injections, using a 5 µm Spherisorb CN (21.2 mm by 250 mm), eluting with 30/70/chloroform/hexane containing 0.1% triethylamine at 20 mL/minute to give (E)-1-[4-(10-diethylaminodecoxy)phenyl]-1,2-diphenyl-2-chloro-ethylene and (Z)-1-[4-(10-diethylaminodecoxy)phenyl]-1,2-diphenyl-2-chloro-ethylene.

EXAMPLE 43

(E)-1-[4-(10-Diethylaminodecoxy)phenyl]-1,2-diphenyl-2-chloro-ethylene citrate salt

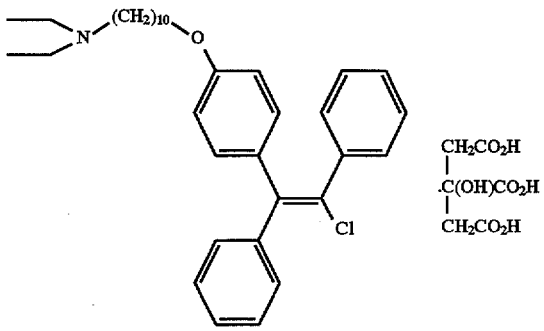

The citrate salt is formed in butanone (2 mL) using (E)-1-[4-(10-diethylaminodecoxy)phenyl]-1,2-diphenyl-2-chloro-ethylene (0.092 g) and citric acid (0.034 g) in butanone (0.5 mL) to give the title compound: mp; 94°–95° C.

EXAMPLE 44

(Z)-1-[4-(10-Diethylaminodecoxy)phenyl]-1,2-diphenyl-2-chloro-ethylene citrate salt

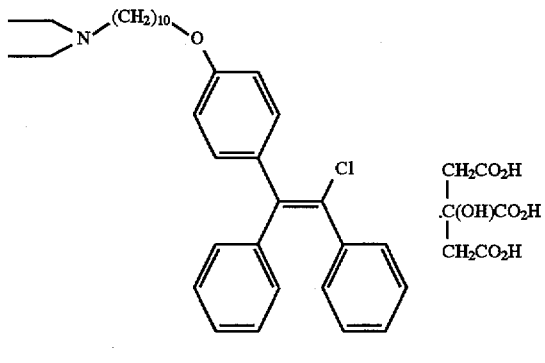

The citrate salt is formed in butanone (0.5 mL) using (Z)-1-[4-(10-diethylaminodecoxy)phenyl]-1,2-diphenyl-2-chloro-ethylene (0.046 g) and citric acid (0.017 g) in butanone (0.5 mL) to give the title compound: mp; 89°–90° C.

EXAMPLE 45

(E and Z)-1-[4-(11-Diethylaminoundecoxy)phenyl]-1,2-diphenyl-2-chloro-ethylene

Prepare by the methods taught in Example 29, using 11-diethylaminoundecanol, and Example 30 to give the title compound. Separate the isomers by HPLC using multiple injections, using a Lichrosorb RP-18 column (21 mm by 250 mm), eluting with methanol containing 0.05% triethylamine at 20 mL/minute to give (E)-1-[4-(11-diethylaminoundecoxy)phenyl]-1,2-diphenyl-2-chloro-ethylene and (Z)-1-[4-(11-diethylaminoundecoxy)phenyl]-1,2-diphenyl-2-chloro-ethylene.

EXAMPLE 46

(E)-1-[4-(11-Diethylaminoundecoxy)phenyl]-1,2-diphenyl-2-chloro-ethylene citrate salt

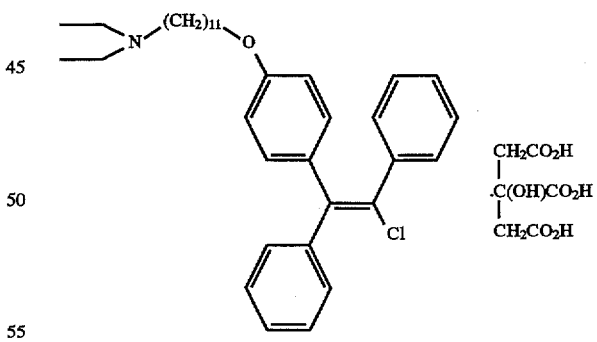

The citrate salt is formed in butanone (2 mL) using (E)-1-[4-(11-diethylaminoundecoxy)phenyl]-1,2-diphenyl-2-chloro-ethylene (0.082 g) and citric acid (0.029 g) in butanone (1 mL) to give the title compound: mp; 104°–105° C.

EXAMPLE 47

(Z)-1-[4-(11-Diethylaminoundecoxy)phenyl]-1,2-diphenyl-2-chloro-ethylene citrate salt

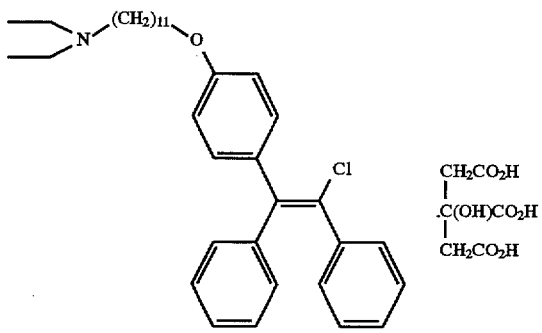

The citrate salt is formed in butanone (2 mL) using (Z)-1-[4-(11-diethylaminoundecoxy)phenyl]-1,2-diphenyl-2-chloro-ethylene (0.0284 g) and citric acid (0.0102 g) in butanone (1 mL) to give the title compound: mp; 89°–92° C.

EXAMPLE 48

(E and Z)-1-[4-(12-Diethylaminododecoxy)phenyl]-1,2-diphenyl-2-chloro-ethylene

Prepare by the methods taught in Example 29, using 12-diethylaminododecanol, and Example 30. Separate the isomers by HPLC using multiple injections, using a Lichrosorb RP-18 column (21 mm by 250 mm), eluting with methanol containing 0.05% triethylamine at 20 mL/minute to give (E)-1-[4-(12-diethylaminododecoxy)phenyl]-1,2-diphenyl-2-chloro-ethylene and (Z)-1-[4-(12-diethylaminododecoxy)phenyl]-1,2-diphenyl-2-chloro-ethylene.

EXAMPLE 49

(E)-1-[4-(12-Diethylaminododecoxy)phenyl]-1,2-diphenyl-2-chloro-ethylene citrate salt

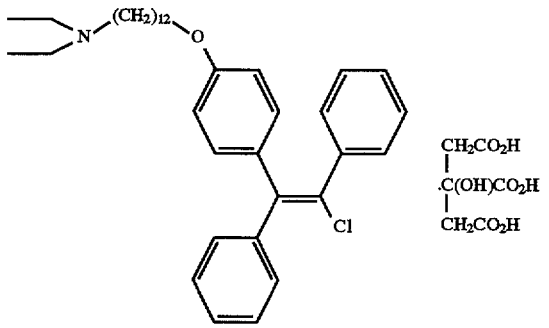

The citrate salt is formed in butanone (2 mL) using (E)-1-[4-(12-diethylaminododecoxy)phenyl]-1,2-diphenyl-2-chloro-ethylene: mp; 96°–98° C., (0.090 g) and citric acid (0.031 g) in butanone (0.5 mL) to give the title compound: mp; 96°–98° C.

EXAMPLE 50

(Z)-1-[4-(12-Diethylaminododecoxy)phenyl]-1,2-diphenyl-2-chloro-ethylene citrate salt

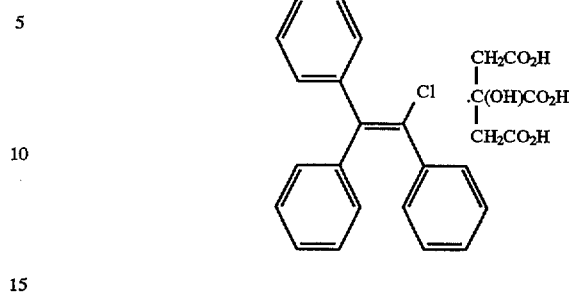

The citrate salt is formed in butanone (2 mL) using (Z)-1-[4-(12-diethylaminododecoxy)phenyl]-1,2-diphenyl-2-chloro-ethylene (0.032 g) and citric acid (0.011 g) to give the title compound: mp; 98°–100° C.

The compounds of Formula I and II which Y is NH and compounds of Formula III and IV can be prepared as described in Scheme C. In Scheme C, compounds which include the alkylene group $(CH_2)_n$ wherein n is an integer from 2 to 12 encompass the compounds of Formula I, II, III, and IV. All substituents, unless otherwise indicated, are previously defined. The reagents and starting materials are readily available to one of ordinary skill in the art.

SCHEME C

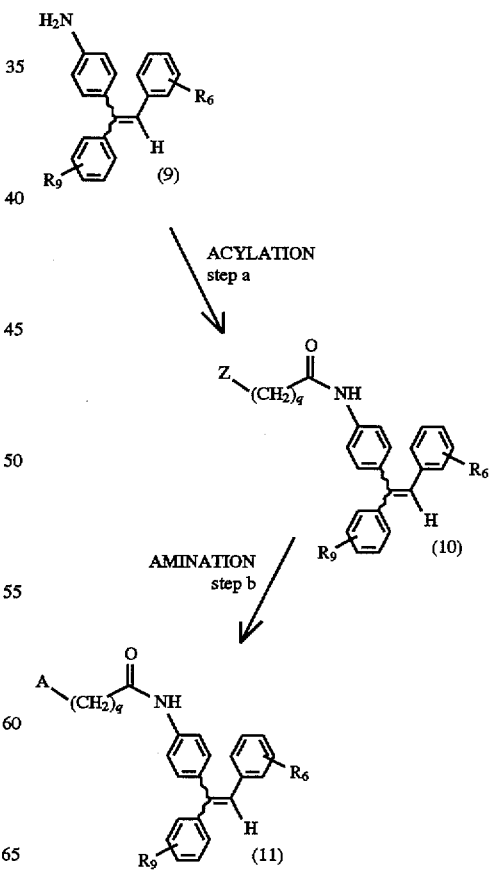

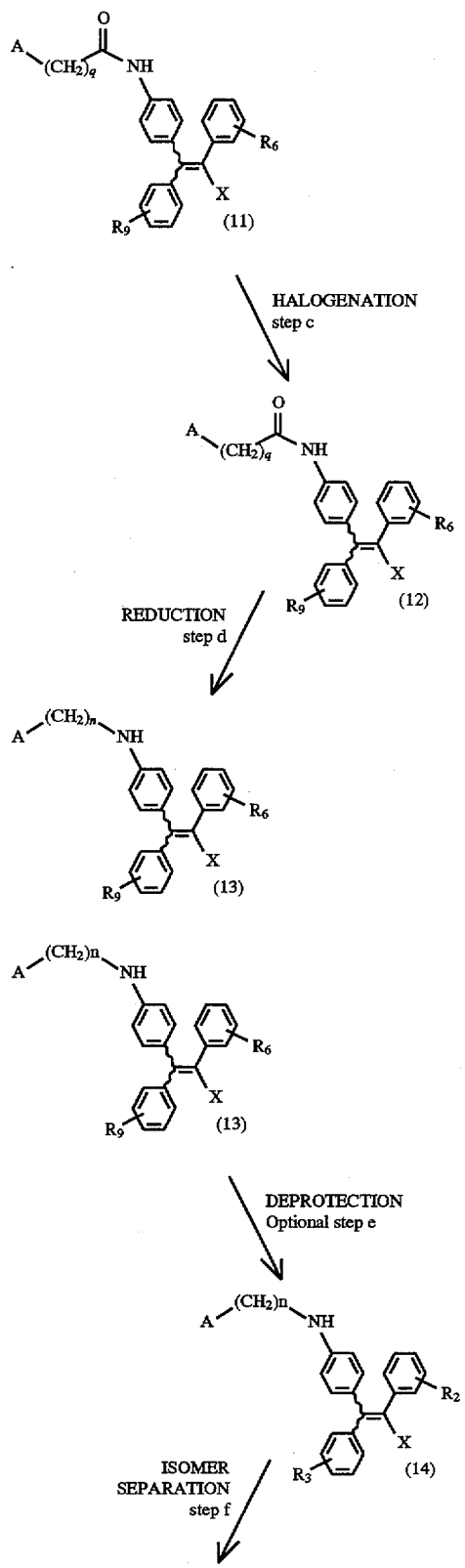

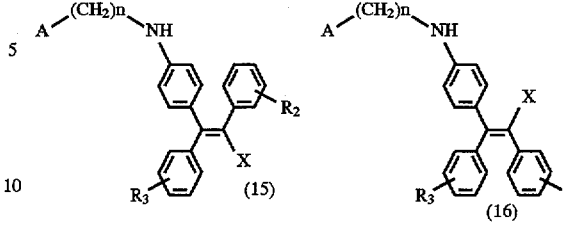

In Scheme C, step a, an appropriate ω-haloalkylacid halide, Z—(CH$_2$)$_q$—C(O)Z$_1$, is added to an appropriate amino-triaryl-ethylene of structure 9 in an acylation reaction to give a ω-haloalkylamido-triaryl-ethylene of structure 10.

An appropriate ω-haloalkylacid halide, Z—(CH$_2$)$_q$—C(O)Z$_1$, is one in which q is 1 less than n, an integer for 2 to 12 as desired in the final product of Formula I, II, III, or IV, and Z and Z$_1$ may each independently be a chlorine atom or a bromine atom. An appropriate amino-triaryl-ethylene of the structure 9 is one in which R$_6$ is R$_2$ as defined above, or is a suitably protected hydroxy which after deprotection provide compounds of Formula I, II, III, or IV in which R$_2$ is a hydroxy group; R$_9$ is R$_3$ as defined above, or is a suitably protected hydroxy which after deprotection provide compounds of Formula I, II, III, or IV in which R$_3$ is a hydroxy group, or R$_9$ is an amino group, a protected amino group, or a group which gives rise to an amino group, such as a nitro group. Appropriate amino-triaryl-ethylenes of the structure 9 are readily prepared by methods analogous to those used to prepare triaryl-ethylene of structure 1 described in U.S. Pat. No. 2,914,563, R. E. Allen et al; U.S. Pat. No. 2,429,556, C. F. Longfellow et al; and *Syn. Comm.* 17, 1787–1796 (1987), M. I. Al-Hassan.

For example, a slight molar excess of a ω-haloalkylacid halide is contacted with a amino-triaryl-ethylene of the structure 9 in a suitable solvent, such as pyridine, dimethylformamide, acetonitrile, or tetrahydrofuran. The reaction is carried out in the presence of a suitable base, such as pyridine, triethylamine, sodium carbonate, or sodium bicarbonate. The reaction may be carried out in the presence of a catalyst, such as 4-dimethylaminopyridine. The reaction is stirred for from 1–72 hours. The production of a compound of Formula I or II in which R$_3$ is —NH(CH$_2$)$_p$A$_1$ wherein p=m and A=A$_1$ or a compound of Formula III or IV in which R$_3$ is —NH(CH$_2$)$_z$A$_1$ wherein z=w and A=A$_1$ requires the use of a compound of structure 1 in which R$_9$ is amino and slightly more than two molar equivalents of a ω-haloalkylacid halide and gives rise to a compound of structure 10 which is a bis-ω-haloalkylamido-triaryl-ethylene. The product can be isolated and purified by techniques well known in the art. For example, the reaction mixture can be concentrated in vacuo to give a residue. The residue can be chromatographed on silica gel using a suitable organic eluent. The material obtained from chromatography can be recrystallized to give a ω-haloalkylamido-triaryl-ethylene of structure 10.

In Scheme C, step b, a ω-haloalkylamido-triaryl-ethylene of structure 10 is contacted in an amination reaction with an appropriate amine, HNRR$_1$, in which R and R$_1$ are as defined above, morpholine, piperidine, piperazine, 4-methylpiparizine, or pyrrolidine to give ω-aminoalkylamido-triaryl-ethylene of structure 11.

For example, a ω-haloalkylamido-triaryl-ethylene of structure 10 is contacted with a large molar excess of an appropriate amine. A large molar excess of amine is used so that the amine also acts as a base to take up the acid liberated in the reaction. The reaction is carried out in a suitable solvent, such as ethanol, methanol, water, ethanol/water mixtures, or methanol/water mixtures. The reaction may be carried out in the presence of a suitable catalyst, such as potassium iodide. The reaction vessel may be sealed to prevent the escape of volatile amines. The reaction mixture is heated to temperatures of from 40° C. to 100° C. For compounds of structure 10 in which $R_9$ is a ω-haloalkylamido group the use of an additional portion of an appropriate amine gives a bis-ω-aminoalkylamido-triaryl-ethylene which gives rise to a compound of Formula I or II in which $R_3$ is —$NH(CH_2)_pA_1$ wherein p=m and A=$A_1$ or a compound of Formula III or IV in which $R_3$ is —$NH(CH_2)_zA_1$ wherein z=w and A=$A_1$. The product is isolated from the reaction zone by evaporation or extraction and is purified by chromatography or salt formation and recrystallization to give a ω-aminoalkylamido-triaryl-ethylene of structure 11.

In Scheme C, step c, a ω-aminoalkylamido-triaryl-ethylene of structure 11 are chlorinated or brominated to give ω-aminoalkylamido-triaryl-ethylene of structure 12.

For example, a ω-aminoalkylamido-triaryl-ethylene of structure 11 is contacted with a molar excess of chlorine, bromine, N-chlorosuccinimide, or N-bromosuccinimide in a solvent, such as chloroform or dichloromethane. The reaction is carried out at temperatures from ambient temperature to the reflux temperature of the solvent. After stirring for from 12–72 hours the product can be isolated and purified by techniques well known in the art. For example, the reaction mixture can be concentrated in vacuo and the product purified by chromatography or by recrystallization to give a ω-aminoalkylamido-triaryl-ethylene of structure 12.

In Scheme C, step d, a ω-aminoalkylamido-triaryl-ethylene of structure 12 is contacted with an appropriate reducing agent in a reduction reaction to give a ω-aminoalkylamino-triaryl-ethylene of structure 13.

An appropriate reducing agent is one that will reduce the amido group of a ω-aminoalkylamido-triaryl-ethylene of structure 12 without effecting the other groups present in the compound. The selection and use of such reducing agents is well known and appreciated in the art.

For example, a ω-aminoalkylamido-triaryl-ethylene of structure 12 is contacted with a molar excess of an appropriate reducing agent, such as lithium aluminum hydride, borane, or borane complexes. The reaction is carried out in a solvent, such as diethyl ether or tetrahydrofuran when the appropriate reducing agent is lithium aluminum hydride, or dichloromethane or chloroform when the appropriate reducing agent is borane. The reaction is carried out at temperatures from ambient temperature to the refluxing temperature of the solvent. For compounds of structure 12 in which $R_9$ is a ω-aminoalkylamido group the use of an additional portion of the appropriate reducing agent gives a bis-ω-aminoalkylamino-triaryl-ethylene which gives rise to a compound of Formula I or II in which $R_3$ is —$NH(CH_2)_pA_1$ wherein p=m and A=$A_1$ or a compound of Formula III or IV in which $R_3$ is —$NH(CH_2)_zA_1$ wherein z=w and A=$A_1$. The product can be isolated from the reaction zone by techniques well known in the art, such as quenching, extraction, and evaporation; and may be purified by methods well known in the art, such as chromatography and recrystallization to give a ω-aminoalkylamino-triaryl-ethylene of structure 13.

In Scheme C, optional step e, for ω-aminoalkylamino-triaryl-ethylene of structure 13 in which $R_6$ or $R_9$ are a protected hydroxy group the protecting group is removed in a deprotection step to provide ω-aminoalkylamino-triaryl-ethylene of structure 14 in which either, $R_2$ or $R_3$, or $R_2$ and $R_3$, are hydroxy as desired in the final product of Formula I or Formula II. Additionally, for ω-aminoalkylamino-triaryl-ethylene of structure 13 in which $R_9$ is a protected amino group is deprotected to provide ω-aminoalkylamino-triaryl-ethylene of structure 14 in which $R_9$ is an amino group can be, by sequentially performing the steps of Scheme C, used as an intermediate for the preparation of a compound of Formula I or II in which $R_3$ is —$NH(CH_2)_pA_1$ wherein p≠n and either A=$A_1$ or A≠$A_1$ or in which $R_3$ is —$NH(CH_2)_pA_1$ wherein p=m and A≠$A_1$ or a compound of Formula III or IV in which $R_3$ is —$NH(CH_2)_zA_1$ wherein z≠w and either A=$A_1$ or A≠$A_1$ or in which $R_3$ is —$NH(CH_2)_zA_1$ wherein z=w and A≠$A_1$. The removal of amine protecting groups utilizing suitable protecting groups such as those described in *Protecting Groups in Organic Synthesis* by T. Greene is well known and appreciated by those skilled in the art.

The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

In Scheme C, step f, the isomers of a ω-aminoalkylamino-triaryl-ethylene of structure 13 or 14 are separated to give a (E)-ω-aminoalkylamino-triaryl-ethylene and the (Z)-ω-aminoalkylamino-triaryl-ethylene.

For example, the isomers of compounds of structure 13 or 14 can be separated and purified by high-performance liquid chromatography or fractional recrystallization of salt to give a (E)-ω-aminoalkylamino-triaryl-ethylene and the (Z)-ω-aminoalkylamino-triaryl-ethylene.

Pharmaceutically acceptable salts of a (E)-ω-aminoalkylamino-triaryl-ethylene and of a (Z)-ω-aminoalkylamino-triaryl-ethylene can be formed in an additional step as is well known and practiced in the art.

The following examples present typical syntheses as described in Scheme C. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "mm" refers to millimeters, "°C." refers to degrees Celsius, "$R_f$" refers to retention factor, "mp" refers to melting point, "HPLC" refers to high performance liquid chromatography.

EXAMPLE 51

(E and Z)-1-[4-N-(4-Chlorobutyrylamino)phenyl]-1,2-diphenyl-ethylene

Combine (E and Z)-1-[(4-amino)phenyl]-1,2-diphenyl-ethylene (0.57 g, 2.1 mmol), 4-chlorobutyryl chloride (0.338 g, 2.4 mmol), and dimethylaminopyridine (10 mg) in pyridine (5 mL). Stir under an inert atmosphere for 16 hours. Evaporate in vacuo to give a residue. Dilute with dichloromethane and extract 3 times with 3M hydrochloric acid solution. Dry the organic layer over $MgSO_4$, filter, and evaporate in vacuo to give the title compound.

EXAMPLE 52

(E and Z)-1-[4-N-(4-Diethylaminobutryrylamino)phenyl]-1,2-diphenyl-ethylene

Combine (E and Z)-1-[4-N-(4-chlorobutyrylamino)phenyl]-1,2-diphenyl-ethylene (3.2 g, 11.8 mmol), diethylamine (30.0 mL), potassium iodide (100 mg, 0.66 mmol), and water (2.0 mL) and seal in a pressure vessel. Heat to 100° C. for 4 hours. Cool to ambient temperature and carefully open the vessel. Evaporate in vacuo. Dilute with dichloromethane and extract with water. Dry the organic layer over $MgSO_4$, filter, and evaporate in vacuo. Chromatograph on silica gel eluting with 10% methanol/ dichloromethane. Combine product containing fractions and concentrate in vacuo to give the title compound.

EXAMPLE 53

(E and Z)-1-[4-N-(4-Diethylaminobutryrylamino)phenyl]-1,2-dipenyl-2-chloro-ethylene Combine (E and Z)-1-[4-N-(4-diethylaminobutyrylamino)phenyl]-1,2-diphenyl-ethylene (1.0 g, 2.4 mmol) and N-chlorosuccinimide (0.80 g, 6.0 mmol) in dichloromethane (15 mL). Heat to reflux and stir at reflux for 48 hours. Cool to ambient temperature. Chromatograph on silica gel eluting with 10% methanol/ dichloromethane. Combine product containing fractions and concentrate in vacuo to give the title compound.

EXAMPLE 54

(E and Z)-1-[4-(4-Diethylaminobutylamino)phenyl]-1,2-diphenyl-2-chloro-ethylene

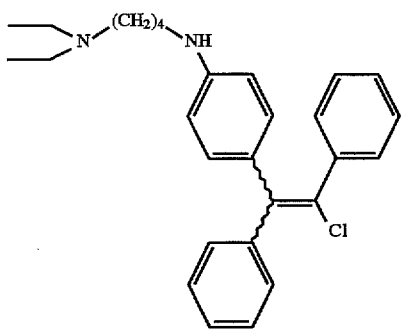

Combine (E and Z)-1-[4-1-(4-diethylaminobutyrylamino)phenyl]-1,2-diphenyl-2-chloro-ethylene (0.55 g, 1.23 mmol) and borane (5 mL, 1M in tetrahydrofuran, 5.0 mmol) in THF (10 mL). Heat to reflux and stir at reflux for 20 hours. Quench with methanol and evaporate in vacuo. Partition between dichloromethane and water. Separate the organic layer and dry over $MgSO_4$, filter and evaporate in vacuo. Chromatograph on silica gel to give the title compound.

The compounds of Formula I and II in which Y is NH and the compounds of Formula III and IV can also be prepared as described in Scheme D. In Scheme D, compounds which include the alkylene group $(CH_2)_n$ wherein n is an integer from 2 to 12 encompass the compounds of Formula I, II, III, and IV. All substituents, unless otherwise indicated, are previously defined. The reagents and starting materials are readily available to one of ordinary skill in the art.

Scheme D

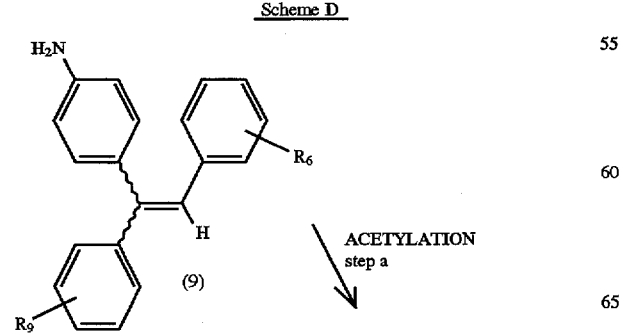

ACETYLATION
step a

Scheme D -continued

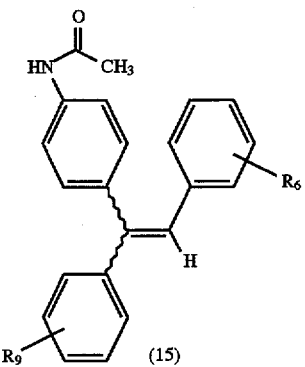

HALOGENATION
step b

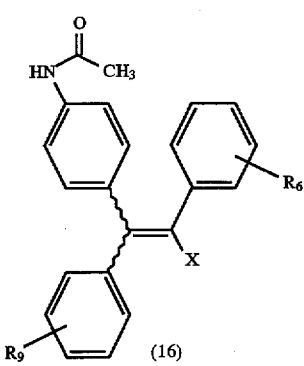

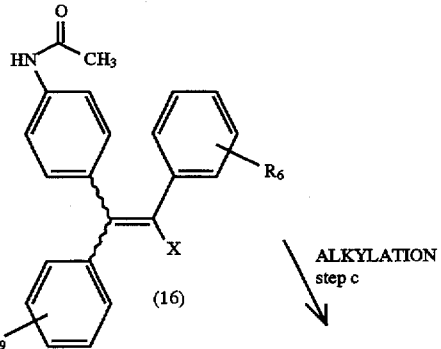

ALKYLATION
step c

-continued
Scheme D

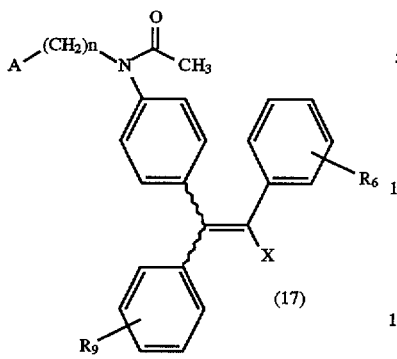

HYDROLYSIS
step d

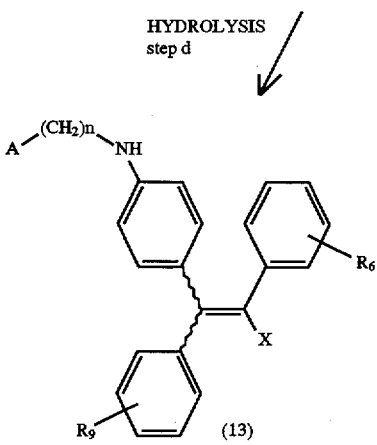

In Scheme D, step a, an appropriate amino-triaryl-ethylene of structure 9 is acetylated to give an acetamido-triaryl-ethylene of structure 15.

An appropriate amino-triaryl-ethylene of structure 9 is as defined above in Scheme C.

For example, an amino-triaryl-ethylene of the structure 9 is contacted with a suitable acetyling reagent, such as acetyl chloride or acetic anhydride. The reaction is carried out in a suitable solvent, such as pyridine, dichloromethane, dimethylformamide, acetonitrile, or tetrahydrofuran. The reaction is carried out in the presence of a suitable base, such as pyridine, triethylamine, sodium carbonate, or sodium bicarbonate. The reaction is stirred for from 1–72 hours. The product can be isolated and purified by techniques well known in the art, such as extraction, evaporation, chromatography, recrystallization, and trituration.

As is appreciated by one of ordinary skill in the art an alcohol precursor to an appropriate amino-triaryl-ethylene of structure 9 can be dehydrated and acetylated in one step to give an acetamido-triaryl-ethylene of structure 15.

In Scheme D, step b, an acetamido-triaryl-ethylene of structure 15 is chlorinated or brominated as generally taught in Scheme C, step c, to give acetamido-triaryl-ethylene of structure 16.

For example, an acetamido-triaryl-ethylene of structure 15 is contacted with a molar excess of chlorine, bromine, N-chlorosuccinimide, or N-bromosuccinimide in a solvent, such as chloroform or dichloromethane. The reaction is carried out at temperatures from ambient temperature to the reflux temperature of the solvent. After stirring for from 12–72 hours the product can be isolated and purified by techniques well known in the art. For example, the reaction mixture can be concentrated in vacuo and the product purified by chromatography or by recrystallization to give a ω-aminoalkylamido-triaryl-ethylene of structure 12.

In Scheme D, step c, an acetamido-triaryl-ethylene of structure 16 is alkylated with an appropriate ω-aminoalkyl halide or a salt thereof to give a N-(ω-aminoalkyl) acetamido-triaryl-ethylene of structure 17.

An appropriate ω-aminoalkyl halide, $A(CH_2)_nZ$, is one in which Z is a chlorine atom, a bromine atom, or a iodine atom; A and n, an integer for 2 to 12 as desired in the final product of Formula I, II, III, or IV.

For example, an acetamido-triaryl-ethylene of structure 16 is contacted with from 1.0 to 10 molar equivalents of an appropriate ω-aminoalkyl halide. The reaction is carried out in the presence of a suitable base, such as sodium ethoxide, sodium methoxide, potassium hydroxide, sodium hydroxide, potassium hydroxide, and sodium carbonate. The reaction is carried out in a solvent, such as ethanol, methanol, tetrahydrofuran, acetone, or butanone. The product may be isolated from the reaction zone by evaporation and extraction and may be purified by methods well known in the art, such as chromatography and recrystallization.

In Scheme D, step d, the acetyl group of a N-(ω-aminoalkyl)acetamido-triaryl-ethylene of structure 17 is hydrolyzed to give an ω-aminoalkylamino-triaryl-ethylene of structure 13. The hydrolysis of acetamido compounds using either basic or acidic conditions is well known and appreciated in the art.

As generally taught in Scheme C, optional step e, an ω-aminoalkylamino-triaryl-ethylene of structure 13 can be deprotected and further modified as required to give a ω-aminoalkylamino-triaryl-ethylene of structure 14.

As generally taught in Scheme C, step f, the isomers of a ω-aminoalkylamino-triaryl-ethylene of structure 13 or 14 are separated to give a (E)-ω-aminoalkylamino-triaryl-ethylene and the (Z)-ω-aminoalkylamino-triaryl-ethylene.

The following examples present typical syntheses as described in Scheme D. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mol" refers to moles, "mL" refers to milliliters, "mm" refers to millimeters, "°C." refers to degrees Celsius, "$R_f$" refers to retention factor, "mp" refers to melting point, "HPLC" refers to high performance liquid chromatography.

EXAMPLE 55

(E and Z)-1-(4-Acetamidophenyl)-1,2-diphenyl-ethylene

Combine 4-aminobenzophenone (50 g, 0.25 mol) and diethyl ether (500 mL). Slowly, add benzylmagnesium chloride (1 L of a 1M solution in diethyl ether over 1.5 hours. After 18 hours, pour the reaction onto ice and an aqueous solution of ammonium chloride. Separate the layers, extract the organic layer with water, dry over $MgSO_4$, filter, and evaporate in vacuo to give a residue. Recrystallize from isopropanol to give 1-(4-aminophenyl)-1,2-diphenyl-ethanol: mp; 105°–107° C.

Combine 1-(4-aminophenyl)-1,2-diphenyl-ethanol (40 g, 0.138 mol) and pyridine (75 mL). Slowly add acetic anhydride (50 mL). Heat on a steam bath. After 20 hours, cool and evaporate in vacuo to give a residue. Partition the residue between diethyl ether and water. Separate the layers, extract the organic layer with water, dry over MgSO₄, filter, and evaporate in vacuo to give the title compound.

EXAMPLE 56

(E and Z)-1-(4-Acetamidophenyl)-1,2-diphenyl-2-chloro-ethylene

Combine (E and Z)-1-(4-acetamidophenyl)-1,2-diphenyl-ethylene and acetic acid (250 mL). Slowly add chlorine (350 mL of a 0.46M solution in carbon tetrachloride). After the addition, stir the reaction at ambient temperature for 1 hour and then heat on a steam bath. After 2 hours, cool and evaporate in vacuo to give a residue. Recrystallize the residue from 95% ethanol to give the title compound: mp; 179°–185° C.

EXAMPLE 57

(E and Z)-1-[4-(N-(2-Diethylaminoethyl)acetamidophenyl]-1,2-diphenyl-2-chloro-ethylene Combine (E and Z)-1-(4-acetamidophenyl)-1,2-diphenyl-2-chloro-ethylene (17.4 g, 0.05 mol), 2-diethylaminoethyl chloride hydrochloride (10 g, 0.058 mol) and powdered potassium hydroxide (6.7 g, 0.12 mol) in acetone (150 mL). Heat to reflux. After 2 hours, filter, and evaporate to give a residue. Partition the residue between diethyl ether and water. Separate the layers, extract the organic layer with water, dry over MgSO₄, filter, and evaporate in vacuo to give the title compound.

EXAMPLE 58

(E and Z)-1-[4-(2-Diethylaminoethylamino)phenyl]-1,2-diphenyl-2-chloro-ethylene citrate salt

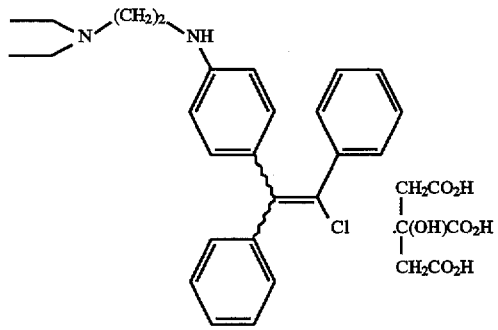

Combine (E and Z)-1-[4-(N-(2-diethylaminoethyl)acetamidophenyl]-1,2-diphenyl-2-chloro-ethylene, aqueous 10% hydrochloric acid (200 mL), and aqueous concentrated hydrochloric acid (10 mL). Heat on a steam bath. After 6 hours, cool to ambient temperature. After 18 hours, add aqueous 10% sodium hydroxide until the solution becomes basic. Extract the basic solution with diethyl ether. Extract the organic layer with water, dry over MgSO₄, filter and evaporate in vacuo to give a residue. Combine the residue and butanone. Add citric acid (4.3 g) to give a solid. Filter and recrystallize twice from butanone to give the title compound: mp; 121°–125° C.

The compounds of Formula I and II in which Y is NH and the compounds of Formula III and IV can be prepared as described in Scheme E. In Scheme E, compounds which include the alkylene group $(CH_2)_n$ wherein n is an integer from 2 to 12 encompass the compounds of Formula I, II, III, and IV. All substituents, unless otherwise indicated, are previously defined. The reagents and starting materials are readily available to one of ordinary skill in the art.

Scheme E

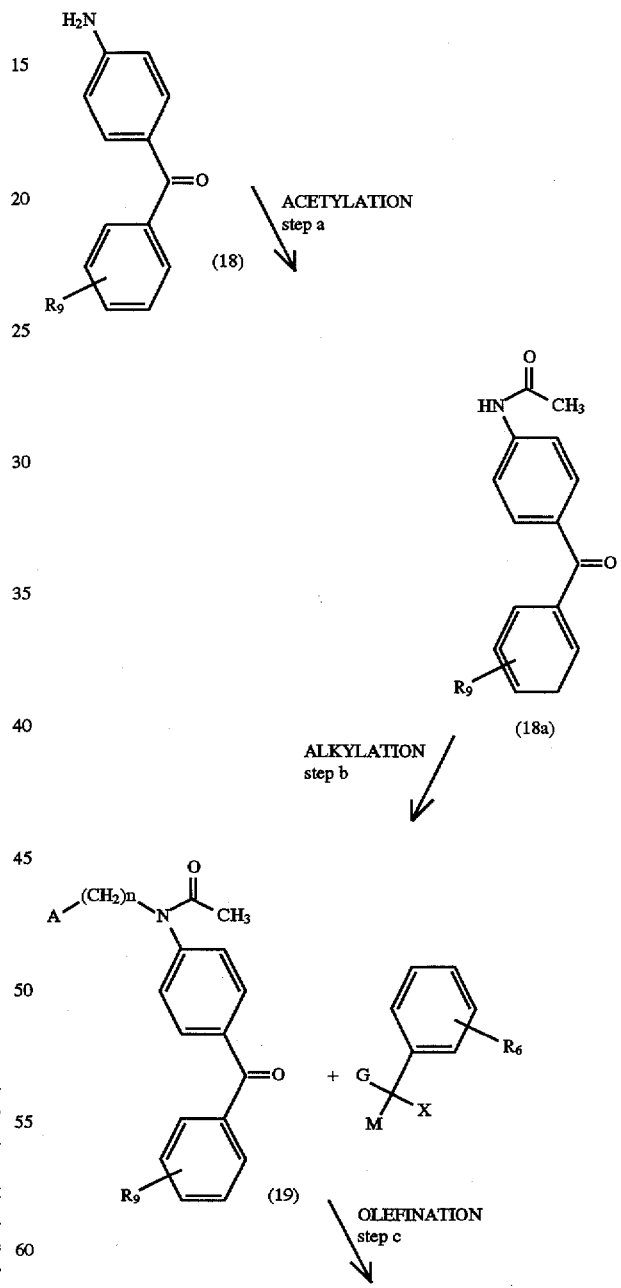

-continued
Scheme E

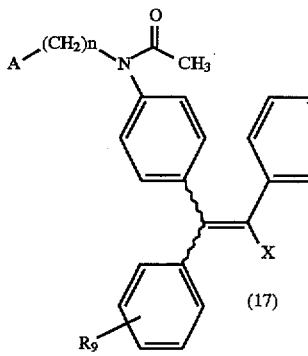

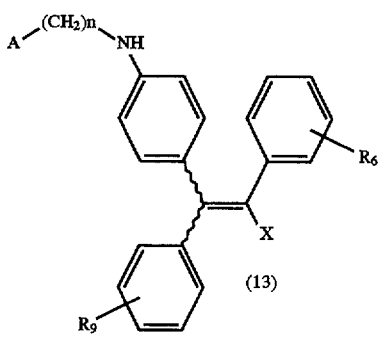

In Scheme E, step a, an appropriate 4-aminobenzophenone of structure 18 is acetylated to give an N-acetyl-4-aminobenzophenone of structure 18a. As is appreciated by those of ordinary skill in the art groups other than acetyl may be used, such as trifluoroacetyl, benzoyl, methanesulfonyl, or trifluoromethanesulfonyl. An appropriate 4-aminobenzophenone of structure 18 is one in which $R_9$ is as defined above in Scheme C, step a.

For example, an appropriate 4-aminobenzophenone of structure 18 is contacted with a suitable acetyling reagent, such as acetyl chloride or acetic anhydride. The reaction is carried out in a suitable solvent, such as pyridine, dichloromethane, dimethylformamide, acetonitrile, toluene, or tetrahydrofuran. The reaction is carried out in the presence of a suitable base, such as pyridine, triethylamine, sodium carbonate, or sodium bicarbonate. The reaction is stirred for about 1–72 hours. Generally, the reaction is carried out at temperatures of from about −20° C. to the refluxing temperature of the solvent. The product can be isolated and purified by techniques well known in the art, such as extraction, evaporation, chromatography, recrystallization, and trituration.

In Scheme E, step b, the N-acetyl-4-aminobenzophenone of structure 18a is alkylated with an appropriate ω-aminoalkyl halide to give an N-ω-aminoalkyl-N-acetyl-4-aminobenzophenone of structure 19. An appropriate ω-aminoalkyl halide, $A(CH_2)_nZ$, is one as described in Scheme D, step c.

For example, a N-acetyl-4-aminobenzophenone of structure 18a is contacted with from 1.0 to 10 molar equivalents of an appropriate ω-aminoalkyl halide. The reaction is carried out in the presence of a suitable base, such as sodium ethoxide, sodium methoxide, potassium hydroxide, sodium hydroxide, potassium carbonate, and sodium carbonate. The reaction is carried out in a solvent, such as ethanol, methanol, tetrahydrofuran, acetone, or butanone. The product may be isolated from the reaction zone by evaporation and extraction and may be purified by methods well known in the art, such as chromatography and recrystallization.

In Scheme E, step c, a N-ω-aminoalkyl-N-acetyl-4-aminobenzophenone of structure 19 is olefinated using an appropriate α-chloro or α-bromo phosphorous reagent to give a N-(ω-aminoalkyl)acetamido-triaryl-ethylene of structure 17.

An appropriate α-chloro or α-bromo phosphorous reagent is one which $R_6$ is as defined in Scheme C, step a, X is chloro or bromo, M is lithium, sodium, or potassium, and G is $P(Ph)_3$, $P(O)(OPh)_2$, $P(O)(OCH_2CH_3)_2$, $P(O)(OCH_3)_2$, or $P(O)(OCH(CH_3)_2)_2$. The preparation and use of appropriate α-chloro or α-bromo phosphorous reagents well known and appreciated in the art, such as described in K. Lee et al., Syn. Comm. 22 649–655 (1992); J. Petrova et al., Synthesis 658–660 (1975); M. D. Crenshaw and H. Zimmer J. Org. Chem. 48 2782–2784 (1983); T. Gajda, Synthesis 717–718 (1990); T. Gajda, Phosphorous and Sulfur 53 327–331 (1990); and S. K. Chakoborty and R. Engle, Syn. Comm. 21 1039–1046 (1991). An appropriate α-chloro or α-bromo phosphorous reagent can be prepared and isolated or isolated and purified before use or can be prepared and used without isolation.

For example, a N-ω-aminoalkyl-N-acetyl-4-aminobenzophenone of structure 19 is contacted with a slight excess of lithium diethyl α-chloro benzylphosphonate. The reaction is carried out in a suitable solvent, such as THF, benzene or toluene. The reaction is performed at temperatures from −78° C. to the refluxing temperature of the solvent. The product can be isolated as generally taught in Scheme D, step c.

Alternately, a N-ω-aminoalkyl-N-acetyl-4-aminobenzophenone of structure 19 is contacted with a slight excess of an anion derived from a α-chloro benzyltriphenylphosphonium salt. The reaction is carried out in a suitable solvent, such as THF, or toluene. The reaction is performed at temperatures from −78° C. to the refluxing temperature of the solvent. The product can be isolated as generally taught in Scheme D, step c.

As generally taught in Scheme D, step d, the acetyl group of a N-(ω-aminoalkyl)acetamido-triaryl-ethylene of structure 17 is hydrolyzed to give an ω-aminoalkylamino-triaryl-ethylene of structure 13.

As generally taught in Scheme C, optional step e, an ω-aminoalkylamino-triaryl-ethylene of structure 13 can be deprotected and further modified as required to give a ω-aminoalkylamino-triaryl-ethylene of structure 14.

As generally taught in Scheme C, step f, the isomers of a ω-aminoalkylamino-triaryl-ethylene of structure 13 or 14 are separated to give a (E)-ω-aminoalkylamino-triaryl-ethylene and the (Z)-ω-aminoalkylamino-triaryl-ethylene.

EXAMPLE 59

N-Acetyl-4-aminobenzophenone

Combine 4-aminobenzophenone (10.0 g, 50.8 mmol), acetic anhydride (5.74 mL, 60.9 mmol), and triethylamine (9.5 mL, 68.5 mmol) in toluene (30 mL). Heat to reflux. After 2 hours, cool to ambient temperature and pour the reaction mixture into water. Stir to give a solid. Collect the solid by filtration, rinse with water, and dry. Recrystallize from acetonitrile to give the title compound. $R_f$=0.35 (silica gel, ethyl acetate).

EXAMPLE 59.1

N-Acetyl-4-aminobenzophenone

Combine 4-aminobenzophenone (500 g, 2.54 mol) and triethylamine (307 g, 3.03 mol) in dichloromethane (2.54 L). Add acetic anhydride (313.9 g, 3.07 mol). After 18 hours, add methanol (100 mL) and evaporate in vacuo to give a residue. Combine the residue and water (8 L) and stir to give a solid. Collect the solid by filtration, rinse repeatedly with water, and dry to give the title compound.

EXAMPLE 60

N-(2-Diethylaminoethyl)-N-acetyl-4-aminobenzophenone

Combine N-acetyl-4-aminobenzophenone (4.0 g, 16.7 mmol), 2-diethylaminoethyl chloride hydrochloride (3.97 g, 23.1 mmol), and powdered potassium hydroxide (2.81 g, 50.1 mmol) in acetone (30 mL). Heat to reflux. After 2 hours, cool and decant the solvent. Evaporate the solvent in vacuo to give a residue. Partition the residue between water and ethyl acetate. Separate the organic layer and extract with water. Dry the organic layer over $MgSO_4$, filter, and evaporate in vacuo to give the title compound: $R_f$=0.0–0.14 (streaks on silica gel, ethyl acetate).

EXAMPLE 60.1

N-(2-Diethylaminoethyl)-N-acetyl-4-aminobenzophenone

Combine N-acetyl-4-aminobenzophenone (250 g, 1.05 mol), 2-diethylaminoethyl chloride hydrochloride (207.5 g, 1.20 mol), and 85% potassium hydroxide (140 g, 2.12 mol) in acetone (3 L). Heat to reflux. After 2 hours, cool and filter. Evaporate the filtrate in vacuo to give a residue. Combine the residue and t-butyl methyl ether (1 L) and water (2 L). Add aqueous 1M hydrochloric acid solution until the pH is about 2.5. Separate the aqueous layer and extract several times with t-butyl methyl ether. Adjust the pH of the aqueous layer to 10 using aqueous 50% sodium hydroxide solution. Extract the aqueous layer twice with dichloromethane. Dry the combined dichlormethane layers over $MgSO_4$, filter, and evaporate in vacuo to give a residue. Chromatograph the residue on silica gel eluting sequentially with ethyl acetate, 5/95 methanol/ethyl acetate, 10/90 methanol/ethyl acetate to give the title compound: $R_f$=0.36 (silica gel, 2/8/0.1 methanol/ethyl acetate/triethylamine).

EXAMPLE 61

(E and Z)-1-[4-N-Acetyl-N-(2-diethylaminoethylamino) phenyl]-1,2-diphenyl-2-chloro-ethylene Combine diethyl benzylphosphonate (1.23 mL, 5.91 mmol) and anhydrous tetrahydrofuran (9.0 mL). Cool to −78° C. using a dry-ice-acetone bath. Add dropwise over 5 minutes a solution of n-butyllithium (4.73 mL, 2.5M in hexanes, 11.8 mmol). After 30 minutes, add benzenesulfonyl chloride (0.76 mL, 5.9 mmol). Add N-(2-diethylaminoethyl) -N-acetyl-4-aminobenzophenone (1.0 g, 2.96 mmol) in anhydrous tetrahydrofuran (6.0 mL). After 5 minutes at −78° C., warm to ambient temperature. After 30 minutes, add a saturated aqueous solution of ammonium chloride (20 mL) and extract with ethyl acetate. Separate the organic layer and extract with a saturated aqueous solution of sodium bicarbonate, dry the organic layer over $MgSO_4$, filter, and evaporate in vacuo to give a residue. Chromatograph the residue on silica gel eluting with 5/94.9/0.1 methanol/ethyl acetate/triethylamine to give the title compound (>2.5/1 E/Z): $R_f$=0.27 (silica gel, 20/80/0.05 methanol/ethyl acetate/triethylamine).

EXAMPLE 61.1

(E and Z)-1-[4-N-Acetyl-N-(2-diethylaminoethylamino) phenyl]-1,2-diphenyl-2-chloro-ethylene Combine diethyl benzylphosphonate (42.9 g, 187 mmol) and anhydrous tetrahydrofuran (350 mL). Cool to −60° C. Add dropwise a solution of n-butyllithium (150 mL, 2.5M in hexanes, 375 mmol) while maintaining the temperature at less than about −55° C. After 30 minutes, add a solution of benzenesulfonyl chloride (32.8 g, 187 mmol) in tetrahydrofuran (90 mL) while maintaining the temperature at less than about −55° C. After 15 minutes, warm the reaction mixture to −30° C. After 15 minutes, cool to −55° C. Add by cannula to a cooled (−55° C.) solution of N-(2-diethylaminoethyl)-N-acetyl-4-aminobenzophenone (55.0 g, 163 mmol) in anhydrous tetrahydrofuran (280 mL). The addition by cannula is carried out while maintaining the temperature of the reaction mixture at less than about −45° C. After 10 minutes, warm slowly to ambient temperature. After 30 minutes, add a saturated aqueous solution of ammonium chloride (500 mL) and extract with ethyl acetate (2.5 L). Separate the organic layer and extract with a saturated aqueous solution of sodium bicarbonate, dry over $MgSO_4$, filter, and evaporate in vacuo to give a residue. Chromatograph the residue on silica gel eluting sequentially with 99.9/0.1 ethyl acetate/triethylamine and 5/94.9/0.1 methanol/ethyl acetate/triethylamine to give the title compound.

EXAMPLE 62

(E and Z)-1-[4-N-(2-Diethylaminoethylamino)phenyl]-1,2-diphenyl-2-chloro-ethylene

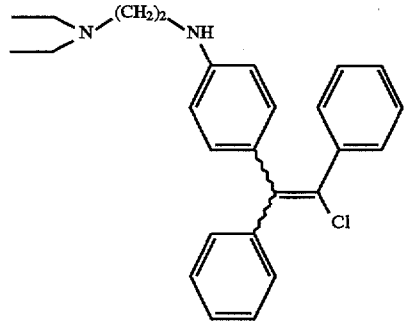

Combine (E and Z)-1-[4-N-acetyl-N-(2-diethylaminoethylamino)phenyl]-1,2-diphenyl-2-chloro-ethylene (0.1 g, 0.22 mmol), potassium t-butoxide (0.16 g, 1.45 mmol), water (8.1 μL, 0.45 mmol), and diethyl ether (1 mL). Heat to reflux. After 16 hours, cool to ambient temperature, pour into ice-water and extract with ethyl acetate. Separate the organic layer and extract with water and saturated aqueous sodium chloride. Dry the organic layer over $MgSO_4$, filter, and evaporate in vacuo to give a residue. Chromatograph the residue on silica gel eluting with 5/94.9/0.1 methanol/ethyl acetate/triethylamine to give the title compound (>2.5/1 E/Z): $R_f$=0.18 (silica gel, 20/80/0.05 methanol/ethyl acetate/triethylamine).

EXAMPLE 62.1

(E and Z)-1-[4-N-(2-Diethylaminoethylamino)phenyl]-1,2-diphenyl-2-chloro-ethylene Combine (E and Z)-1-[4-N-acetyl-N-(2-diethylaminoethylamino)phenyl]-1,2-diphenyl-2-chloro-ethylene (59.3 g, 133 mmol), potassium t-butoxide (95 g, 850 mmol), water (2.0 mL), and tetrahydrofuran (1.0 L).

Heat to reflux. After 1 hour, cool to ambient temperature and partition between water and ethyl acetate. Separate the organic layer and extract with water and saturated aqueous sodium chloride. Dry the organic layer over $MgSO_4$, filter, and evaporate in vacuo to give the title compound.

EXAMPLE 63

(E)-1-[4-N-(2-Diethylaminoethylamino)phenyl]-1,2-diphenyl-2-chloro-ethylene hydrochloride salt

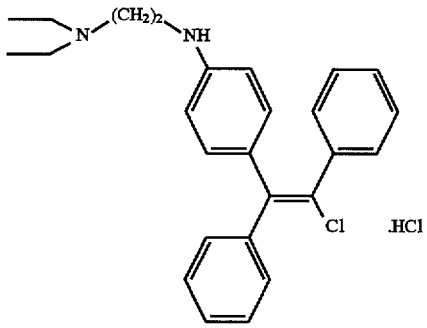

Combine (E and Z)-1-[4-N-acetyl-N-(2-diethylaminoethylamino)phenyl]-1,2-diphenyl-2-chloro-ethylene (53.9 g, 133 mmol) and diethyl ether. Cool to about −5° C. Add hydrochloric acid (gas, 10.1 g, 280 mmol) over about 5 minutes while maintaining the temperature at about 5°–15° C. to give a solid. Collect the solid by filtration, rinse with diethyl ether, and dry. Combine the solid and acetone (375 mL). Heat to reflux. After 1.5 hours, cool to ambient temperature and collect the solid by filtration, rinse with acetone. Combine the solid with tetrahydrofuran (450 mL) and heat to reflux. After 18 hours, cool to ambient temperature and collect the solid by filtration, rinse with tetrahydrofuran. Again combine the solid with tetrahydrofuran (400 mL) and heat at reflux. After 18 hours, cool to ambient temperature and collect the solid by filtration, rinse with tetrahydrofuran, and dry in vacuo to give the title compound (98.9% E-isomer).

EXAMPLE 64

(E)-1-[4-N-(2-Diethylaminoethylamino)phenyl]-1,2-diphenyl-2-chloro-ethylene citric acid salt

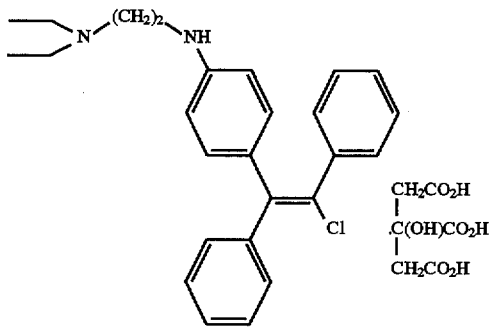

Combine (E)-1-[4-N-acetyl-N-(2-diethylaminoethylamino)phenyl]-1,2-diphenyl-2-chloro-ethylene hydrochloride salt (27.6 g, 58 mmol) and ethyl acetate (350 mL). Carefully add with stirring a saturated aqueous solution of sodium bicarbonate (200 mL). After 30 minutes, separate the organic layer and extract with a saturated aqueous solution of sodium chloride. Combine the aqueous layers and extract with ethyl acetate. Dry the combined organic layers over $MgSO_4$, filter, and evaporate in vacuo to give a residue. Combine the residue and acetone (300 mL), filter, and add a solution of citric acid (11.1 g, 57.8 mmol) in acetone (70 mL). Stir for 5 hours to give a solid. Collect the solid by filtration, rinse with acetone, and dry in vacuo to give the title compound. Elemental Analysis calculated for $C_{26}H_{28}ClN_2 \cdot C_6H_8O_7$: C, 64.37; H, 6.25; N, 4.69. Found: C, 64.05; H, 6.19; N, 4.59.

EXAMPLE 65

Measurement of the Prevention of Bone Loss

Female, Sprague-Dawley rats weighing 200 to 225 grams each (70–75 days of age) are obtained from Harlan Sprague Dawley, Inc. (Indianapolis, Ind.). For each compound, studies are carried out on four groups of animals as follows: Group 1 consists of 5 to 20 ovariectomized rats treated with test compound at typical doses of 0.001 to 10 mg/kg/day; Group 2 consists of 5 to 20 ovariectomized rats treated with vehicle; Group 3 consists of 5 to 20 sham ovariectomized rats (incision made but ovaries not removed) treated with test compound at typical doses of 0.001 to 10 mg/kg/day; Group 4 consists of 5 to 20 sham ovariectomized rats treated with vehicle. All rats are housed individually in suspended wire cages and provided standard rodent laboratory pellets (Purina #5001) and deionized water adlibitum.

The test compound is homogenized in distilled water containing lecithin (10 mg/ml), sodium methylparaben (1.05 mg/ml) and sodium propylparaben (0.23 mg/ml). Compound and vehicle are administered daily for 40 consecutive days by gavage in a volume of 5 ml/kg. Treatment is initiated on the day following ovariectomy or sham ovariectomy. Twenty-four hours after the final administration of test compound (or vehicle) the rats are sacrificed, the hind limbs removed, dissected free of the bulk of soft tissue and then placed in 10% buffered formalin until further processed. Complete ovariectomy is verified at the time of sacrifice and rats with fragments of ovarian tissue are excluded.

After a minimum of one week in formalin, the femurs and tibias are carefully dissected free of each other and remaining soft tissue. The femurs are then air dried for a minimum of 48 hours and radiographed in a Faxitron X-ray cabinet (Hewlett-Packard, McMinnville Oreg.) using Kodak XK-1 film exposed for 9 seconds at a tube voltage of 60 kV. Images of radiographs are captured using a CCD-72 solid-state video camera (Dage-MTI Inc., Michigan City, Ind.) equipped with a 50 mm (1:1.8) Nikon lens and a +1 or combined +4, +2, and +1 close-up lenses depending on the desired magnification. The captured images are digitized with a CFG framegrabber (Imaging Technology Inc., Bedford Mass.) and analyzed using Optimas image analysis software (Bioscan Inc., Edmonds Wash.).

Bone density (i.e., gray value of radiographic images) is measured at the distal femur. Cancellous bone loss is measured at the proximal tibia. Decreased gray value variance reflects the loss of fine structure of bone present in radiographs.

Image analysis measurements are made as follows: For determination of the gray values of femurs, images are precisely orientated on the monitor using screen templates and analysis region (2.30 mm×3.34 mm; 11250 pixels) is superimposed over the digitized images at the distal femur at approximately 1.2 mm proximal to the border of the medial and lateral condyles. The gray value of each picture element within the analysis region is then measured and the mean gray value calculated by Optimas image analysis software (BioScan Inc; Edmondes, Wash.). To minimize the effect of random noise on gray value measurements, two images of the analysis region are captured and averaged. The averaged image is then treated with a 3×3 smoothing filter to yield the final image for gray value measurements. In addition to mean gray value, gray value variance is also determined at the distal femur using the same analysis region used for determining mean gray value.

To control for variability in gray value measurements potentially arising from the radiographic and imaging procedures, gray values are converted to Density Units using standard curves prepared from gray value measurements collected from a 10-step aluminum wedge radiographed along with the specimens on each film.

After removal from the formalin, tibias are placed in labeled tissue cassettes, decalcified, imbedded in parraffin, cut in 5 micron sagittal sections which are stained with aniline blue (a differential stain for bone). Trabecular bone loss is measured directly from stained sections of the proximal tibia.

For measuring trabecular bone area, tibia section images are precisely orientated on a moniter screen template and a analysis region (1.17 mm×1.54 mm; 18240 pixels) centered over the image between the cortico-medullary margins and positioned 1.0 mm from the growth plate at the closest point. Optimas then determines the area of both the analysis region and the trabecular bone within the region (in mm$^2$) and calculated the percent of the region occupied by trabecular bone.

Statistical comparisons are done using Data Desk Professional software (Odesta Corp., Northbrook Ill.). Comparisons between groups are made using the two-tailed t test for independent means with a pooled estimate of variance. Values for the right and left femurs are averaged for each animal and the combined values used to calculate descriptive statistics and for t tests. Statistical significance is assigned at $P \leq 0.05$ and $P \leq 0.01$.

EXAMPLE 66

Measurement of Serum Osteocalcin

For each compound, studies are carried out on four groups a animals as described in Example 65. Anesthetize each animal with $CO_2$, collect blood by cardiocentesis into clot-activating serum separator tubes. Collect the serum by centrifugation and stored at −20° C.

Serum osteocalcin levels are measured by radioimmunoassay using the method recommended by Biomedical Technologies, Inc. from whom the required reagents are purchased. Serum is diluted 1:20 and either 100 µl of diluted sample or 100 µl rat osteocalcin standard (BT-412) is added to 100 µl of rat osteocalcin primary antibody (goat anti-rat osteocalcin, BT-413), 100 µl normal goat nonimmune serum (NIS) and RIA buffer [122.5 mM NaCl, 25 mM Na$_4$EDTA, 10 mM NaH$_2$PO$_4$, pH 7.4, 0.1% Tween 20 and 0.1% bovine serum albumin (RIA grade)] to give a total volume of 500 µl. Incubate at 4° C. overnight on an orbital platform shaker (120 rpm). The second day, [$^{125}$I]-rat osteocalcin (BT-411R) is added in 100 µl (approximately 20,000 cpm) to compete with bound osteocalcin. Tubes are vortexed, then incubate overnight at 4° C. on an orbital shaker. On day three, 1 ml of precipitating second antibody [2% donkey anti-goat lgG (BT-414) in 0.1M sodium phosphate buffer, pH 7.4, containing 2.5% polyethylene glycol and 0.05% NaN$_3$] is then added. The samples are mixed and incubated for 2 h at 4° C. on an orbital shaker, followed by sedimentation by centrifugation at 1500×g for 15 min at 4° C. The supernatant is carefully discarded and the pellets washed twice by centrifugation with 500 µl distilled water. Supernatant is discarded and the radioactivity associated with the pellet quantitated (2 min) using an LKB gamma counter. Osteocalcin standards run in parallel are used for determination of standard osteocalcin values. Statistical analysis for osteocalcin measurements is carried out using Instat software to do a two-sided T-test.

An embodiment of the present invention provides a method for the treatment of a patient afflicted with bone tissue loss or osteoporosis comprising the administration thereto of a effective antiosteoporosis amount of a compound of Formula I, II, III, or IV.

The terms "bone tissue loss" as used herein refers to a disease or condition in which bone mass or density is decreased by the loss of both mineral and protein matrix components resulting in bone fragility.

The term "osteoporosis" as used herein refers to a disease or condition in which bone tissue loss is responsible for bone fragility resulting in one or more bone fractures.

As used herein, "an effective antiosteoporosis amount" of a compound of Formula I, II, III, or IV refers to an amount which is effective, upon single or multiple dose administration to the patient, in preventing or decreasing the rate of bone tissue loss in the patient beyond that expected in the absence of such treatment.

Identification of patients in need of treatment for bone tissue loss or osteoporosis is well within the ability and knowledge of one skilled in the art. The methods for identification of patients which are at risk of developing bone tissue loss or osteoporosis are known and appreciated in the medical arts, such as family history of the development of bone tissue loss or osteoporosis and the presence of risk factors associated with the development of bone tissue loss or osteoporosis. A clinician skilled in the art can readily identify, by the use of clinical tests, physical examination and medical/family history, those patients who are at risk of developing bone tissue loss or osteoporosis and thus readily determine if an individual is a patient in need of prophylactic treatment for bone tissue loss or osteoporosis.

An effective antiosteoporosis amount can be readily determined by the attending diagnostician, as one skilled in the art, by the use of known techniques and by observing results obtained under analogous circumstances. In determining the effective antiosteoporosis amount or dose a number of factors are considered by the attending diagnostician, including, but not limited to: the species of mammal; its size, age, and general health; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective antiosteoporosis amount of a compound of Formula I, II, III, or IV is expected to vary from about 0.001 milligram per kilogram of body weight per day (mg/kg/day) to about 100 mg/kg/day.

In a further embodiment, the present invention provides for a method of increasing bone mass and preventing bone tissue loss or osteoporosis in a patient, comprising administering an effective antiosteoporosis amount of a compound of the Formula I, II, III, or IV.

As used herein, the term "patient" refers to a warm-blooded animal, such as a mouse, a rat, a hamster, a rabbit, or a human, which is afflicted with bone tissue loss or osteoporosis or is at risk of developing bone tissue loss or osteoporosis or who is in need of treatment for bone tissue loss or osteoporosis.

In effecting treatment of a patient afflicted with the disease states described above or in effecting prophylactic treatment of a patient who may be afflicted with the disease states as described above, a compound of Formula I, II, III, or IV can be administered in any form or mode which makes the compound bioavailable in effective amounts, including oral and parenteral routes. For example, compounds of Formula I, II, III, or IV can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds of Formula I, II, III, or IV can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of Formula I, II, III, or IV in admixture or otherwise in association with one or more inert carriers. These compositions are useful, for example, as assay standards, as convenient means of making bulk shipments, or as pharmaceutical compositions. An assayable amount of a compound of Formula I, II, III, or IV is an amount which is readily measurable by standard assay procedures and techniques as are well known and appreciated by those skilled in the art. Assayable amounts of a compound of Formula I, II, III, or IV will generally vary from about 0.001% to about 75% of the composition by weight. Inert carriers can be any material which does not degrade or otherwise covalently react with a compound of Formula I, II, III, or IV. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective antiosteoporosis amount of a compound of Formula I, II, III, or IV in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 0.1 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of Formulas I and II in their end-use application.

With respect to the substituent X, compounds of Formula I, II, III, and IV wherein X is chloro are generally preferred.

With respect to the substituent A, compounds of Formula I, II, III, and IV wherein A is diethylamino are generally preferred.

What is claimed is:

1. A method of treating bone tissue loss or osteoporosis in a patient, comprising administering an effective antiosteoporosis amount of a compound of the formula

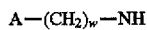
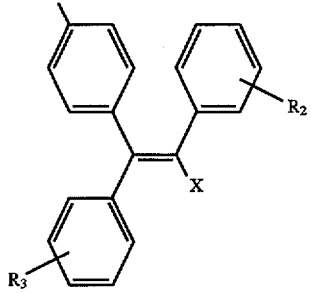

wherein

A is a radical of the formula

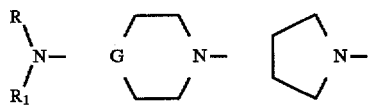

wherein

R and $R_1$ are each independently hydrogen or $C_1$–$C_4$ alkyl; and

G is HN, $H_3$CN, $CH_2$, or O;

w is an integer from 2 to 3;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_z$A$_1$ in which A$_1$ is a radical of the formula

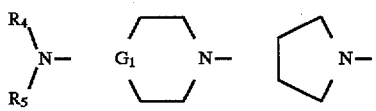

wherein

Y is —HN—;

$R_4$ and $R_5$ are each independently hydrogen or $C_1$–$C_4$ alkyl;

$G_1$ is HN, $H_3$CN, $CH_2$, or O; and z is an integer from 2 to 3;

X is chloro or bromo;

or a pharmaceutically acceptable salt thereof.

2. A method according to claim 1 wherein w is 2.

3. A method according to claim 1 wherein A is the radical

wherein

R and $R_1$ are each independently hydrogen or $C_1$–$C_4$ alkyl.

4. A method according to claim 3 wherein R and $R_1$ are each independently $C_1$–$C_4$ alkyl.

5. A method according to claim 4 wherein R and $R_1$ are each ethyl.

6. A method according to claim 1 wherein $R_3$ is hydrogen.

7. A method according to claim 1 wherein X is chloro.

8. A method according to claim 1 wherein the compound is (E)-1-[4-(2-diethylaminoethylamino)phenyl]-1,2-diphenyl-2-chloro-ethylene.

9. A method of treating bone tissue loss or osteoporosis in a patient, comprising administering an effective antiosteoporosis amount of a compound of the formula

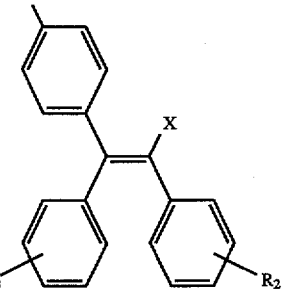

wherein

A is a radical of the formula

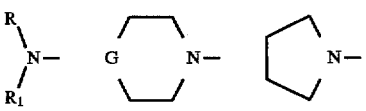

wherein

R and $R_1$ are each independently hydrogen or $C_1$–$C_4$ alkyl; and

G is HN, $H_3$CN, $CH_2$, or O;

w is an integer from 2 to 3;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y(CH$_2$)$_z$A$_1$ in which A$_1$ is a radical of the formula

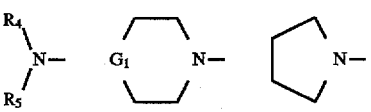

wherein

Y is —HN—;

$R_4$ and $R_5$ are each independently hydrogen or $C_1$–$C_4$ alkyl;

$G_1$ is HN, $H_3$CN, $CH_2$, or O; and z is an integer from 2 to 3;

X is chloro or bromo;

or a pharmaceutically acceptable salt thereof.

10. A method according to claim 9 wherein w is 2.

11. A method according to claim 9 wherein A is the radical

wherein

R and $R_1$ are each independently hydrogen or $C_1$–$C_4$ alkyl.

12. A method according to claim 11 wherein R and $R_1$ are each independently $C_1$–$C_4$ alkyl.

13. A method according to claim 12 wherein R and $R_1$ are each ethyl.

14. A method according to claim 9 wherein $R_3$ is hydrogen.

15. A method according to claim 9 wherein X is chloro.

16. A method according to claim 9 wherein the compound is (Z)-1-[4-(2-diethylaminoethylamino)phenyl]-1,2-diphenyl-2-chloro-ethylene.

* * * * *